United States Patent
Narayan et al.

(10) Patent No.: US 7,569,556 B2
(45) Date of Patent: Aug. 4, 2009

(54) METHOD OF USE OF CARBOXYLATED POLYSACCHARIDES TOPICALLY ON THE EYEBALL

(75) Inventors: Ramani Narayan, Okemos, MI (US); Laura M. Fisher, Dearborn, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 549 days.

(21) Appl. No.: 11/125,444

(22) Filed: May 10, 2005

(65) Prior Publication Data

US 2005/0255143 A1     Nov. 17, 2005

Related U.S. Application Data

(60) Provisional application No. 60/569,723, filed on May 10, 2004.

(51) Int. Cl.
  *A61K 31/715* (2006.01)
  *A61K 31/717* (2006.01)
  *A61K 31/718* (2006.01)
  *C08B 1/00* (2006.01)
  *C08B 33/08* (2006.01)
  *C08B 35/08* (2006.01)
  *C08B 31/18* (2006.01)

(52) U.S. Cl. .............................. 514/57; 514/60; 536/56; 536/104; 536/105

(58) Field of Classification Search ...................... None
See application file for complete search history.

(56) References Cited

U.S. PATENT DOCUMENTS 3,679,795 A * 7/1972 De Somer et al. ............. 514/25
2002/0123470 A1 * 9/2002 Clark .......................... 514/36

OTHER PUBLICATIONS

The Merck Manual of DIagnosis and Therapy, Sixteenth Edition, published 1992 by Merck Research Laboratories, ed. by Berkow et al., pp. 2376-2377.*
Aelenei et al., "Dicarboxycellulose/streptomycin Complex as a pH-Sensitive Device for Controlled Release of Streptomycin" Analele Stiintifice ale Universitatii "Al. I. Cuza" din Iasi, Chimie (2000) vol. 8 No. 1, pp. 9-14.*

* cited by examiner

*Primary Examiner*—Shaojia Anna Jiang
*Assistant Examiner*—Eric S Olson
(74) *Attorney, Agent, or Firm*—Ian C. McLeod

(57) ABSTRACT

The use of chemically modified dicarboxy polysaccharides for the topical treatment of the eyeball are described. The modified polysaccharides provide a carrier in solutions for the treatment of the eyeball to obtain a timed release.

18 Claims, 19 Drawing Sheets

Structure I      Structure II      Structure III

METHOD OF USE OF CARBOXYLATED POLYSACCHARIDES TOPICALLY ON THE EYEBALL

CROSS-REFERENCE TO RELATED APPLICATIONS

This application claims priority to U.S. provisional application Ser. No. 60/569,723, filed May 10, 2004.

STATEMENT REGARDING FEDERALLY SPONSORED RESEARCH OR DEVELOPMENT

Not Applicable

STATEMENT REGARDING GOVERNMENT RIGHTS

Not Applicable

BACKGROUND OF THE INVENTION (1) Field of the Invention

The present invention relates to the use of groups chemically modified polysaccharides which have carboxylic acid on the eyeball. The composition provides a timed release of the medicament on the outside of the eyeball.

(2) Description of the Related Art

The prior art describes various compositions derived from natural carbohydrates for use as carriers and processes for the preparation of modified carbohydrates, particularly cellulose. Natural polymers and gums have been used in pharmaceutical formulations of sustained-release carriers, and modified celluloses, carboxy methylcellulose (CMC) and modified methyl cellulose (MMC) are found in a large number of formulations as viscosity enhancers. Because of their wide acceptance of these modified natural polymers, pharmaceutical companies are interested in the use of modified natural polymers for their drug delivery systems. Natural polymers with gelling properties that have been successfully used in topical formulations include gellan gum and carrageenans. Topical formulations with gelling properties afford increased ocular bioavailability of certain drugs.

The literature and patents show that much of the focus is centered around natural polymers. GELRITE, a registered trademark of Monsanto, is used by Merck (Radway, N.J.) in a preparation of timolol, TIMOPTIC XE. This is the only known in situ gelling drug delivery system currently on the market. It is a low-acetyl gellan gum which would have a structure similar to FIG. 3 and can ionically crosslink in the presence of a divalent cation such as calcium. Rozier et al (International Journal of Pharmaceutics 57:163-168 (1989) has shown that in in vivo testing GELRITE behaved similar to HEC (hydroxyethycellulose), a known viscosity enhancer. It significantly reduced intraocular pressure over the HEC and this was determined to be caused by an increased residence time at the surface of the eye.

Another natural gel-forming polysaccharide is alginate. Cohen et al (Opthalmic Delivery System. US, Teva Pharmaceutical Industries (1998)) describe an alginate system that gels in the presence of calcium ions in the eye. Alginate is a mixture of guluronic and mannuronic acids. They suggest using a mixture with the guluronic acid concentrations higher than 65% to form a suitable gel. When testing pilocarpine, a common glaucoma treatment, the alginate formulated system demonstrated a correlation between the gelation capability of the alginate formulation and the speed at which it occurs and the sustained release properties. It was also claimed that there was excellent ocular tolerance in the test rabbits; even though redness of the conjunctivae was reported for 1-2 hours after instillation of the drops.

A final natural polysaccharide that can form gels in situ is pectin. The pectin was isolated from Aloe Vera, which contains a higher galacturonic acid ration will form a gel when subjected to mono- or divalent ions at a low pectin of concentration of 0.25% w/v. It will also form a gel in the presence of small organic compounds, proteins, nucleic acid, and live cells.

GELFOAM, a structured matrix of gelatin, has been studied for the release of pilocarpine. The matrix is a structured water-insoluble sponge prepared from purified pork skin gelatin that will biodegrade. Because this simple matrix released most of the drug within 15 minutes, retardants had to be added. This matrix embedded in cetyl ester wax demonstrated zero-order release kinetics while the matrix impregnated with polyethylene glycol 400 monostearate exhibited close to first-order kinetics. The results show that gelatin itself does not provide for good sustained release. The following table summarizes work in ocular drug delivery systems.

TABLE 3

Ocular drug delivery systems

| Matrix Material | Method of Action | Author |
| --- | --- | --- |
| Natural Polymers | | |
| Alginate | Ionic concentration | Cohen (Cohen 1998) |
| Gellan Gum | Ionic concentration | Rozier (Rozier, Mazuel et al. (1989) |
| Pectin | Ionic concentration | NI (Ni and Yates (2002) |
| Gelatin | Not in situ gelation | Nadkarni (Hadkarni and Yalkowsky (1993) |
| Cyclodextrins | Not in situ gelation | |
| Synthetic Polymers | | |
| Poloxamer | Temperature change | Lin (Lin and Sung 2003) |
| Pluronic | Temperature change | Lin (Lin and Sung 2003) |
| Carbopol | pH change | Lin (Lin and Sung 2003) |
| Cellulose acetophthalate | pH change | Gurney (Gurney 1986) |

Many synthetic polymers have been tested for sustained release in the eye. While they have the advantage of being engineered to specific applications, their breakdown products are not always known, which can lead to extended FDA testing. The prior art has described a formulation approach of combining Carbopol and Pluronic. Carbopol is a high molecular weight carboxy vinyl polymer and Pluronic is a class of block copolymers containing polyoxyethylene and polyoxypropylene. This formulation claims to be free-flowing at non-physiological conditions (pH 4.0 and 25° C.), but forming a gel at physiological conditions (pH 7.4 and 37° C.). A disadvantage to this system is the high amount of Pluronic (14%) required for optimal gel formation. Again there are many disadvantages of synthetic polymers including high polymer concentration, irritancy and potentially harmful breakdown products.

Objects

It is an object of the present invention to provide modified polysaccharides for topical use on the eyeball. This and other objects will become increasingly apparent by reference to the following description.

SUMMARY OF THE INVENTION

The present invention relates to a method for providing a topical timed release of a medicament for the eyeball of an animal including humans or other mammals in need thereof, which comprises: providing a composition which comprises: a medicament; and a chemically modified polysaccharide (CMP) comprising linked saccharide rings with ring opened saccharide units at $C_2$ and $C_3$ bond and containing carboxylic acid moieties or water dispersible salt as a random copolymer wherein the CMP is water dispersible to form a clear solution as a time release adjuvant for the medicament; and topically providing the medicament on the eyeball to provide the timed release.

The present invention particularly relates to a pharmaceutical composition for topical treatment of the eyeball which comprises: a medicament for the eyeball; and a chemically modified polysaccharide (CMP) comprising linked saccharide rings with ring opened saccharide units at $C_2$ and $C_3$ bond and containing carboxylic acid moieties or water dispersible salt as a random copolymer wherein the CMP is water dispersible to form a clear solution as a time release adjuvant for the medicament onto the eyeball.

Preferably in the CMP all or portions of $C_2$ and $C_3$ is a hydroxyl group other than at units which have carboxylic acid group. Most preferably, in the CMP both $C_2$ and $C_3$ are carboxylic acid groups. Preferably the CMP is a copolymer of linked units of the formula:

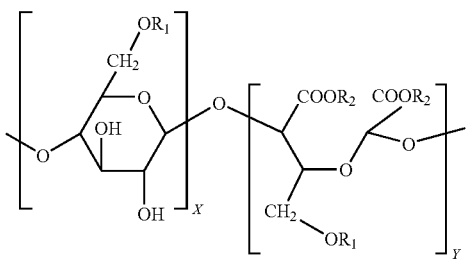

wherein ring opened units in the copolymer are between 10 to 90 mole percent, wherein $R_1$ is H or COOR where R is alkyl or aryl, and wherein $R_2$ is H, alkyl or an aryl group containing 1 to 12 carbon atoms. Preferably the animal is a mammal. Preferably the mammal is human.

A pharmaceutical composition for topical treatment of the eyeball which comprises:
 (a) a medicament for the eyeball; and
 (b) a chemically modified polysaccharide (CMP) comprising linked saccharide rings with ring opened saccharide units at $C_2$ and $C_3$ bond and containing carboxylic acid moieties or water dispersible salt as a random copolymer wherein the CMP is water dispersible to form a clear solution as a time release adjuvant for the medicament onto the eyeball.

DESCRIPTION OF PREFERRED EMBODIMENTS

The present invention provides a flexible, water dispersible, biocompatible material for the topical treatment of the eyeball. It was determined that engineering carboxy groups onto a natural polysaccharide backbone was used to provide a water dispersible biocompatible material. Starch and cellulose were chosen as the polysaccharide backbone because of their abundance and their current acceptance in other pharmaceutical applications. The engineering of the carboxy starch with rigid sugar units and flexible chain segments carrying carboxy groups and being water soluble or dispersible is novel. Application of these oxidized polysaccharides to drug delivery systems for the eye is also novel. Different methods of oxidation are known, including the use of sodium periodate, hypochlorite, or ozone. All of these methods can be used separately or combined until the desired material properties are achieved. Oxidation by sodium periodate was preferred research because it has the best method to control the position and extent of oxidation.

Figure 1:
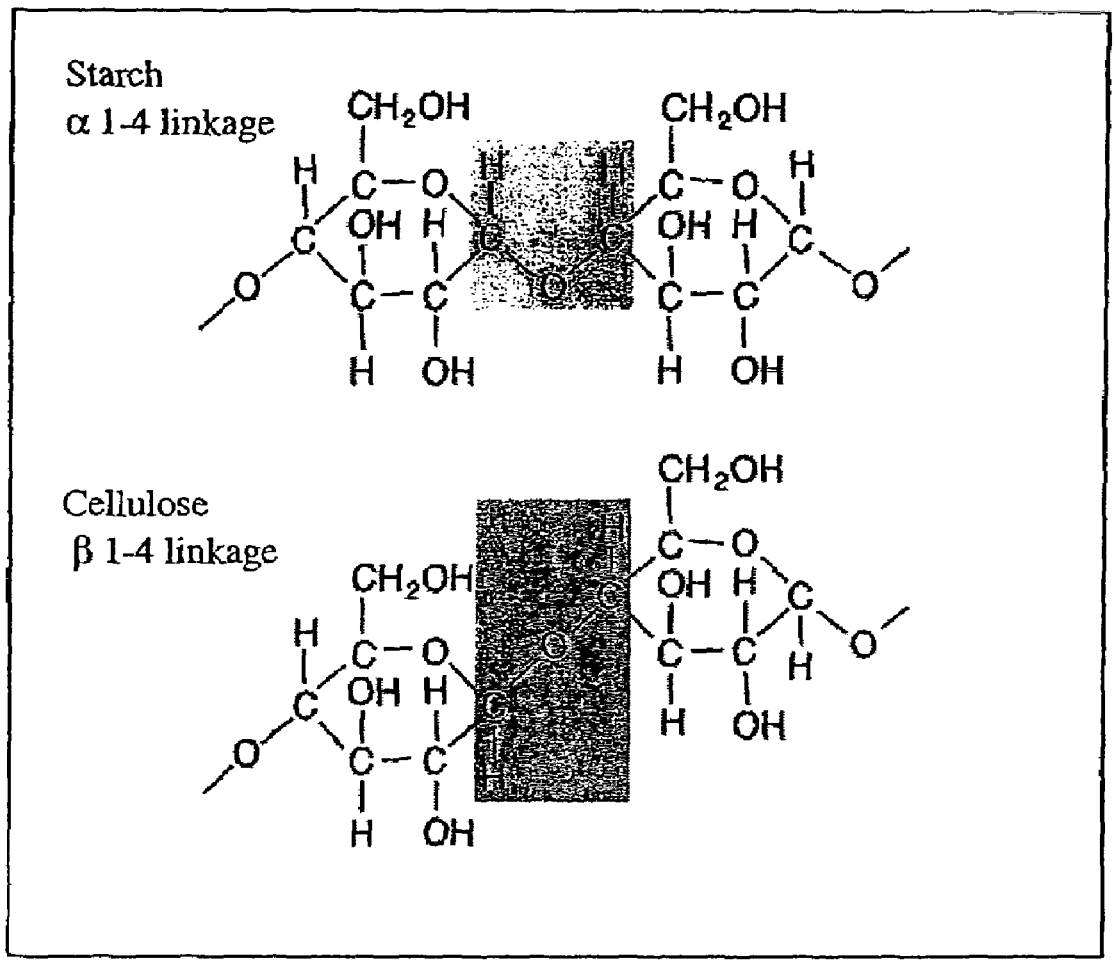
FIG. 1 shows the structures of starch and cellulose.

Cellulose and starch both consist of repeating glucose units with only the glycosidic bond differing as seen in FIG. 1. The oxidation methods could be applied to either structure, although there are differences in the kinetics because of the structure of the materials. Starch is composed of amylose that forms a helical structure. When the material is hydrated, the helices open and water can penetrate the material easily. Cellulose, on the other hand, forms a tight crystalline structure that is not as easily hydrated.

Figure 2:
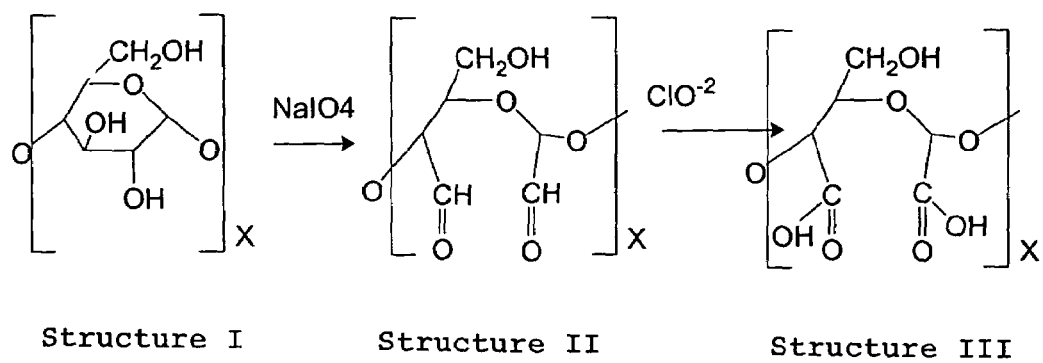
FIG. 2 shows a reaction scheme oxidation of starch.

In the periodate method, the starch/cellulose ring is opened between the C-2 and C-3 using $NaIO_4$ in the first step (Floor, M., L. P. M. Hofsteede, W. P. T. Groenland, L. A. Th.Verhaar, A. P. G. Kieboom, H. van Bekkum: Preparation and calcium complexation of oxidized polysaccharides. II: Hydrogen peroxide as co-reactant in the chlorite oxidation of dialdehyde glucans. Recl. Trav. Chim. Pays-Bas. (1989), 108, 384-392) which forms an aldehyde structure. Secondly, the dialdehyde is oxidized using any oxidizing agent (i.e. NaOCl) and carboxyl groups will be formed at the C-2 and C-3 (see FIG. 2.

In this method, by controlling the amount of ring opening, the total amount of carboxylation can be controlled. Floor (Floor, M., L. P. M. Hofsteede, W. P. T., Groenland, L. A. Th.Verhaar, A. P. G. Kieboom, H. van Bekkum: Preparation and calcium complexation of oxidized polysaccharides. II: Hydrogen peroxide as co-reactant in the chlorite oxidation of dialdehyde glucans. Recl. Trav. Chim. Pays-Bas. (1989), 108, 384-392) described a process where the second step oxidation uses hydrogen peroxide as an inexpensive HOCl scavenger that will reduce the HOCl. The reaction is as follows:

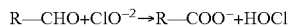

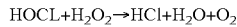

This was an important improvement over previous methods which used $ClO^{-2}$ as a scavenger. Besides being less toxic and less expensive, (Floor, M., L. P. M. Hofsteede, W. P. T., Groenland, L. A. Th.Verhaar, A. P. G. Kieboom, H. van Bekkum: Preparation and calcium complexation of oxidized polysaccharides. II: Hydrogen peroxide as co-reactant in the chlorite oxidation of dialdehyde glucans. Recl. Trav. Chim. Pays-Bas. (1989), 108, 384-392) reports that this method gives higher yields of the dicarboxy polysaccharide with superior calcium sequestering properties as compared to the reactions using chlorite as the scavenger.

Figure 3:
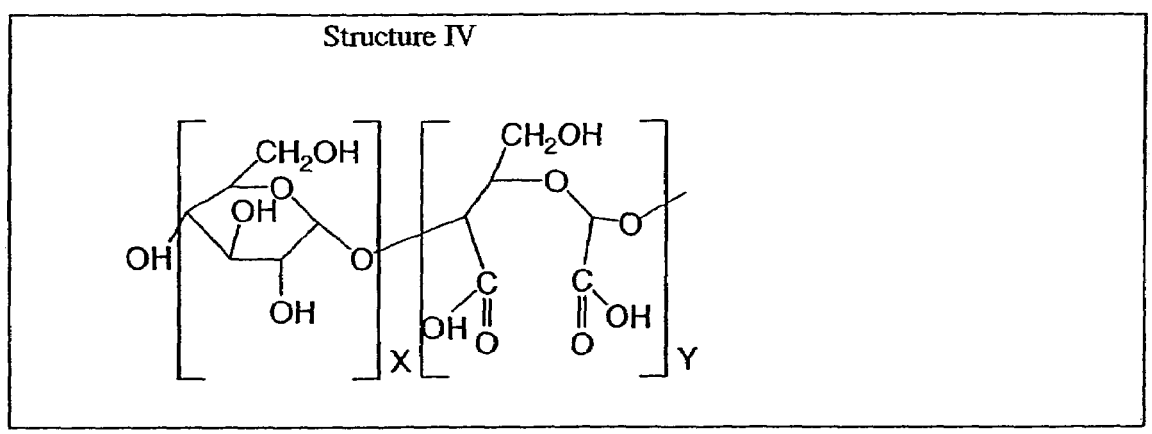
FIG. 3 shows a copolymer starch structure.
Figure 4:
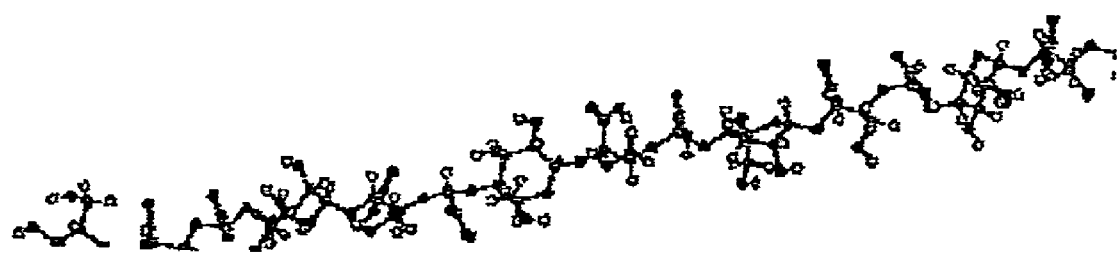
FIG. 4 shows 3D structure of 50% dicarboxy starch.

By controlling the amount, nature, and conditions of oxidation or hydrolysis, the percent carboxyl groups incorporated, the position of attachment, and the molecular weight can be controlled. By effectively controlling the first periodate oxidation step, copolymers can be formed that contain both the structure of the glucose ring and the flexibility of the open ring structure with —COOH groups on them (structure IV), as shown in FIG. 3.

A completely flexible copolymer structure can be engineered by partial oxidation of the —CHO groups to —COOH and reducing the remaining aldehyde groups to —OH using sodium borohydride.

The dicarboxy polysaccharides are stable at the alkaline pH of the washing process but are degraded under the acidic wastewater (pH 4-5) conditions due to their polyacetal structure. The resulting mono- and oligomeric fragments are readily biodegradable but will not form the structure needed for this application. Floor (Floor, M., L. P. M. Hofsteede, W. P. T., Groenland, L. A. Th.Verhaar, A. P. G. Kieboom, H. van Bekkum: Preparation and calcium complexation of oxidized polysaccharides. II: Hydrogen peroxide as co-reactant in the chlorite oxidation of dialdehyde glucans. Recl. Trav. Chim. Pays-Bas. (1989), 108, 384-392) shows that at a pH=3 the dicarboxy starch can degrade up to 80% in 24 hours, while at a pH=7 it will only degrade 20% over a 24 hour period. This is important to note since ophthalmic solutions are usually formulated around pH=7.4. Also, this shows that the modified starch can be easily hydrolyzed. Erythronic and glyoxylic acids are the principal acidic hydrolysis fragments with minor amounts of glycolic, oxalic and formic acids. This indicates the C2-C3 dicarboxy polysaccharide structure stays intact (Floor, M., L. P. M. Hofsteede, W. P. T., Groenland, L. A. Th.Verhaar, A. P. G. Kieboom, H. van Bekkum: Preparation and calcium complexation of oxidized polysaccharides. II: Hydrogen peroxide as co-reactant in the chlorite oxidation of dialdehyde glucans. Recl. Trav. Chim. Pays-Bas. (1989), 108, 384-392).

These carboxylated cellulosic derivatives can form gels with the addition of divalent cations, such as $Ca^{+2}$. The rate of gelation, the gel strength and the release profile are controlled by percent carboxyl group engineered onto the polymer chain, its position on the polymer chain, and the molecular weight of the polymer chain. Floor (Floor, M., L. P. M. Hofsteede, W. P. T., Groenland, L. A. Th.Verhaar, A. P. G. Kieboom, H. van Bekkum: Preparation and calcium complexation of oxidized polysaccharides. II: Hydrogen peroxide as co-reactant in the chlorite oxidation of dialdehyde glucans. Recl. Trav. Chim. Pays-Bas. (1989), 108, 384-392) has also shown that the calcium complexing properties does not differ with respect to the type of glycosidic bond (i.e. the β-1-4 linkages of cellulose compared to the α 1-4 linkages of starches). It is also important to note that the calcium complexing ability is strongly dependent on the molecular weight in the region $M_w$ $10^4$ to $10^5$ and at least an $M_w$ of $10^5$ is required for superior calcium complexation.

Figure 5:
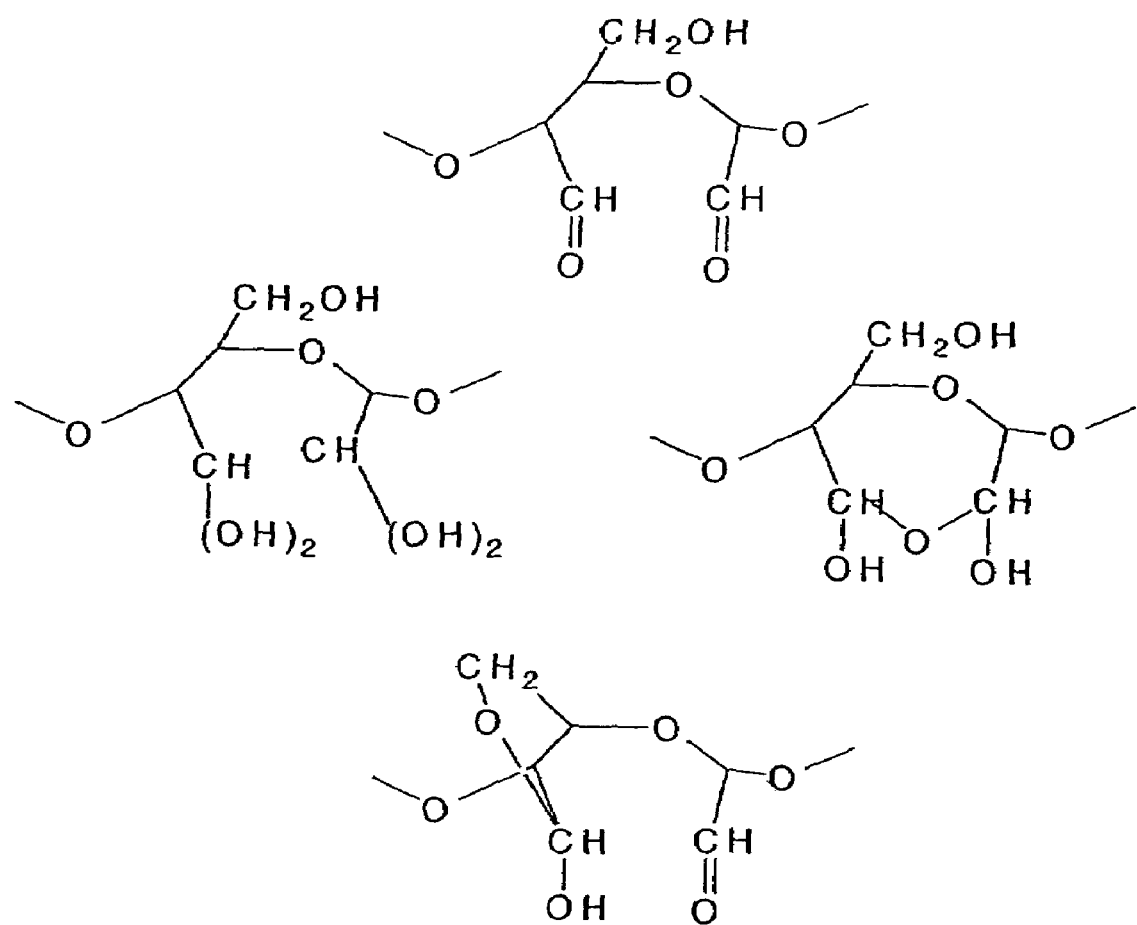
FIG. 5 shows possible structures of periodate-oxidized starch. 1) free aldehyde 2) hydrated aldehyde 3) hemialdol 4) hemiacetal.

The dialdehyde reaction can lead into other formations including a hydrated aldehyde, a hemiacetal, or a hemiadol (Fan, Q. C., D. Lewis et al., Journal of Applied Polymer Science 82:1195-1202 (2001)). The structures of these are shown in FIG. 5.

The periodate reaction is light sensitive and, therefore, care was taken to exclude light. While, some authors (Besemer, A. C., A. E. J. deNooy et al., Abstracts of Papers of the American Chemical Society 212 21-Cell (1996); deNooy, A. E. J., A. C. Besemer et al., Zuckerindustrie 122(2):126-127 (1997); Kim, U. J., S. Kuga et al., Biomacromolecules 1(3):488-492 (2000)) suggest running the reaction at room temperature or colder, (Narayan, R., Conversion of Cellulose and Xylan into Glycols. 1983, Laboratory of Renewable Resources Engineering, Purdue University, NSF Final Report) reported the reaction could be run at slightly elevated temperatures with little interference from side reactions. For the following Examples, the periodate reaction was run at 40° C. Concentrations were used that were similar to earlier work by the prior art.

It was first proposed (Narayan, R., Conversion of Cellulose and Xylan. into Glycols, 1983, Laboratory of Renewable Resources Engineering, Purdue University, NSF Final Report) that the periodate oxidation of cellulose follow the rate law:

$$r = -\frac{d[P]}{dt} = \frac{K_1[P][C]}{K^{-1}+[P]}$$

This rate law was explained by being consistent with a mechanism involving the formation of an intermediate cellulose-periodate complex, most likely a cellulose-periodate cyclic diester which would then slowly decompose to the final products.

Later an improved explanation of the starch oxidation by periodate was proposed. It has been suggested that the kinetecs follow a $2^{nd}$ order dependence at t=0, then change to another model at approximately t=10 minutes (Veelaert, S., D. Dewit et al., Polymer 35(23):5091-5097 (1994)). This work was conducted using granular potato starch and HPLC for analysis, an improvement method over previous papers which used titration to analyze the dialdehyde formed.

Veelaert et al propose that after 5 to 10 minutes the reaction deviates from second order kinetics because of the polymeric structure of the material and the possibility of hemiacetal or acetal formation. The following two rate laws are defined for free and inhibited anhydroglucose units (an acetal neighbor):

$$\frac{d[X]}{dt} = k_1 \mu^2 [S_o]([P_o] - [X])$$

$$\frac{d[X]}{dt} = k_2 \mu (1-\mu)[S_o]([P_o] - [X])$$

Where [X]=the erythritol concentration at any time
 [$S_o$]=the initial starch concentration expressed as total initial anhydroglucose units
 [$P_o$]=initial periodate concentration
 μ=1-degree of oxidation (1−X/g)

These two equations are combined and from experimental data they observed that $\kappa_2$ was much smaller than $\kappa_1$. The previous formulas then can be simplified into:

$$\frac{d[X]}{dt} = \frac{k_1}{[S_o]}([S_o] - [X])^2([P_o] - [X])$$

Analytical Methods

FTIR

A PERKINS ELMER SYSTEM 2000FTIR was used to characterize samples. The samples were pressed in KBR pellets and run for 16 scans. The wavelength range was 4000 $cm^{-1}$ to 400 $cm^{-1}$.

Titration

Sodium hydroxide was used to titrate against the COOH groups. The sodium hydroxide was standardized against potassium acid phthalate to obtain its normality. It was titrated to an endpoint indicated by phenolphthalein. A concentration of approximately 1-5 wt % was used. Because of the viscous nature of the material, the indicator didn't react very quickly a false endpoint would show up. The protocol used was if the indicator stayed pink (acid) for 15 minutes without lightening it was considered the endpoint.

ESEM

An environmental scanning electron microscope was used to characterize the structure of the material. The instrument is an ELECTROSCAN 2020 environmental scanning electron microscope. For these samples, there was a beam voltage of 25 kV with an emission current of 49 uA. The water pressure was varied from 2 Torr to 9 Torr.

Dicarboxy Matrix Synthesis and Characterization Oxidation Methods:

First the method of oxidation was examined. The following three methods were used with the native starch.

Method I

TABLE 4

Explanation of Oxidation Methods

| | | Reaction Time | Results |
|---|---|---|---|
| Method 1 | 1-step oxidation with sodium hypochlorite | 24 hours | Completely water soluble product that is extremely hydroscopic in the presence of air. Also yellows when exposed to air. |
| Method 2 | 1-step oxidation with ozone | 6 hours | Non-water soluble product that shows very little carboxyl peaks in IR. |
| Method 3a | 2-step oxidation with sodium m-periodate followed by sodium chlorite | 6 hours + 12-24 hours | Gummy product that is soluble in water. Swells quickly when rewetted. |
| Method 3b | Same as above, except that special care was taken to keep the dialdehyde from drying out in between reactions | 3 hours + 6 hours | Gummy product that is soluble in water Swells quickly when rewetted |

Figure 6:
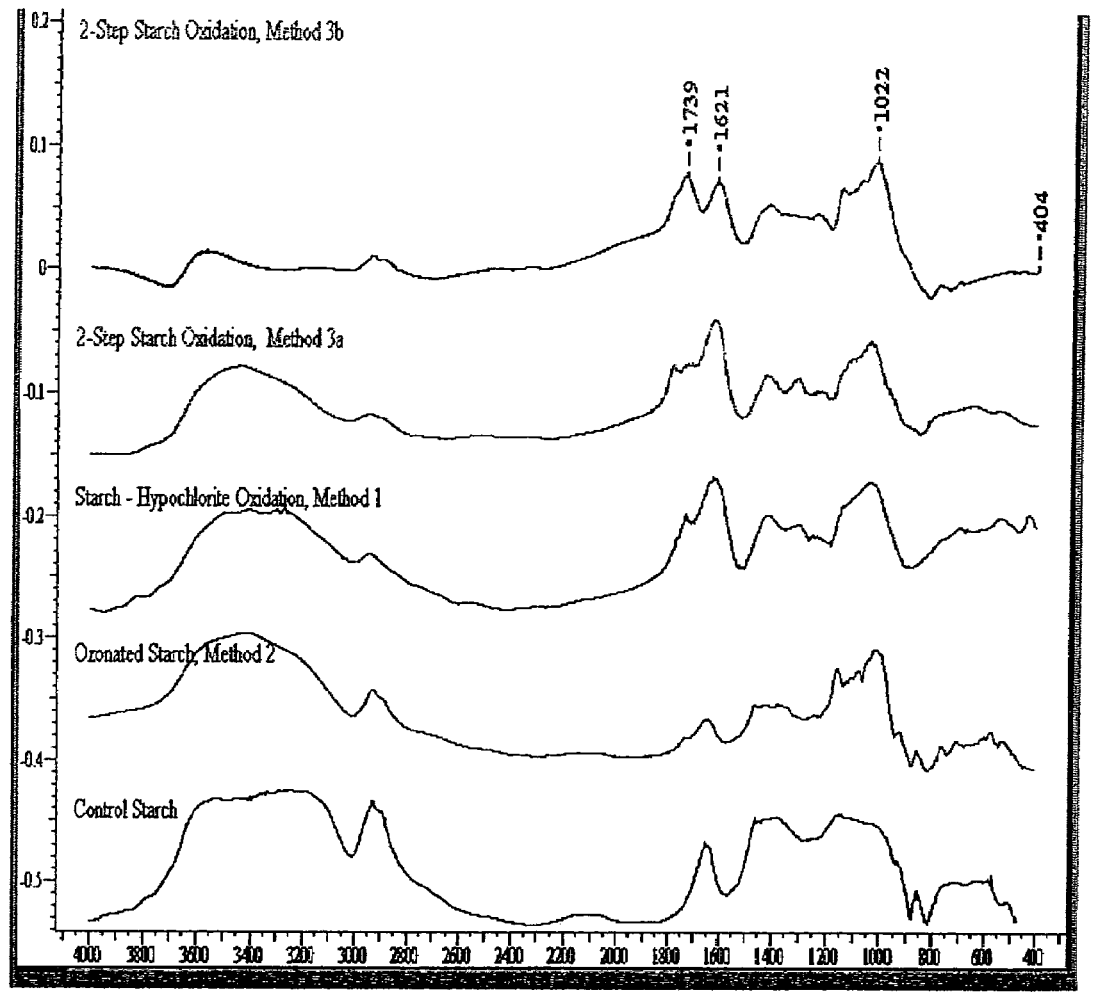
FIG. 6 shows a FTIR Comparison of oxidation methods.
Figure 7:
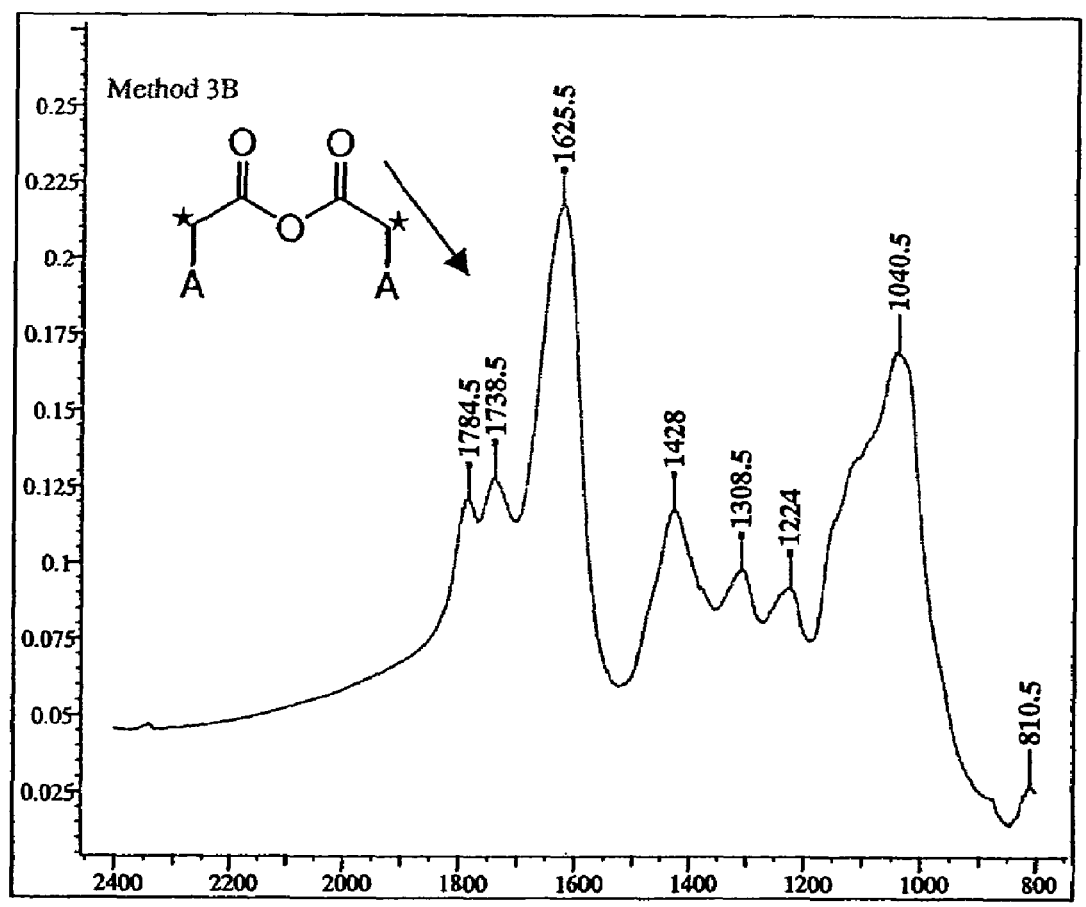
FIG. 7 shows a FTIR of a possible oxidized hemialdol structure.

From the FTIR in FIG. 6, the carbonyl stretch around 1740 $cm^{-1}$ shows that the different methods had different impacts on oxidation. While not quantitative, its comparison can be made by comparing it to the neighboring 1620 $cm^{-1}$ (C—OH) peak. The ozonated starch, so a very slight shoulder around 1740 $cm^{-1}$ indicating that there was some reaction. The hypochlorite method and Method 3a show that there is slightly more carbonyl present but the peak is much smaller than the 1620 $cm^{-1}$. These lead to the possibility that the water solubility of the material may be due to hydrolysis of the starch as opposed to too high a carboxyl presence. As seen in the top peak, there is a high level of carboxyl and the peak is stronger than the 1620 $cm^{-1}$ peak. The difference between the 3a and the 3b method, which in this case had the exact same reactant concentrations, indicates that the structure of the dialdehyde product before the second oxidation plays a very important role in the subsequent oxidation. While this example did not indicate some of the reactions so a presence of an aldol reaction. As seen in FIG. 7, the additional peak at 1784 $cm^{-1}$ indicates the presence of an anhydride which could indicate the presence of the hemi-aldol structure. Specifically a strong anhydride of the structure R—COOCO—R shows a carbonyl stretch at 1790-1740 $cm^{-1}$. This would be consistent of the oxidation of the hemi-aldol structure.

Polysaccharide Choice

Oxidation Method 3a was tried on different saccharides including native corn starch, waxy starch, cellulose, pretreated cellulose, xylans and glucose. The native and waxy starch produced the best results. The cellulose produced similar results but the reaction time was longer and required pretreatment with a strong acid. Because of that the starch was used in subsequent reactions. The following chart summarizes the results of the products.

TABLE 5

The results of the oxidation of different saccharides.

| Material | Comments | Periodate Oxidation Reaction time | Chlorite Oxidation Reaction Time | Results |
|---|---|---|---|---|
| Native Starch | | 6 hours | | Good results, high dicarboxy content, material swells |
| Waxy starch | Waxy pearl 1108 | 6 hours | | Good results, high dicarboxy content, material swells |
| Cellulose | Sigmacell from Sigma-Aldrich | 24 hours | | Only small percentage was oxidized |
| Pretreated Cellulose | Sigmcell pretreated with phosphoric acid and sodium hydroxide | 24 hours | | Good results, high dicarboxy content, material swells |
| Glucose | | 24 hours | | Material was over oxidized |
| Xylans | | 7 hours | | No change in the material |

Titration

Titration with sodium hydroxide was used to measure the amount of carboxyl groups present in the samples. All of the values reported are in terms of carboxyl groups/anhydrogluco ring. For example 100% would indicate that every anhydrogluco ring has one carboxyl group present. Theoretically, the maximum value would be 300% since the C-2, C-3 and C-6 carbon could potentially contain a carboxyl group. Besides actual content, the titration also could be used to quantify the reproducibility of the reaction.

Figure 8:
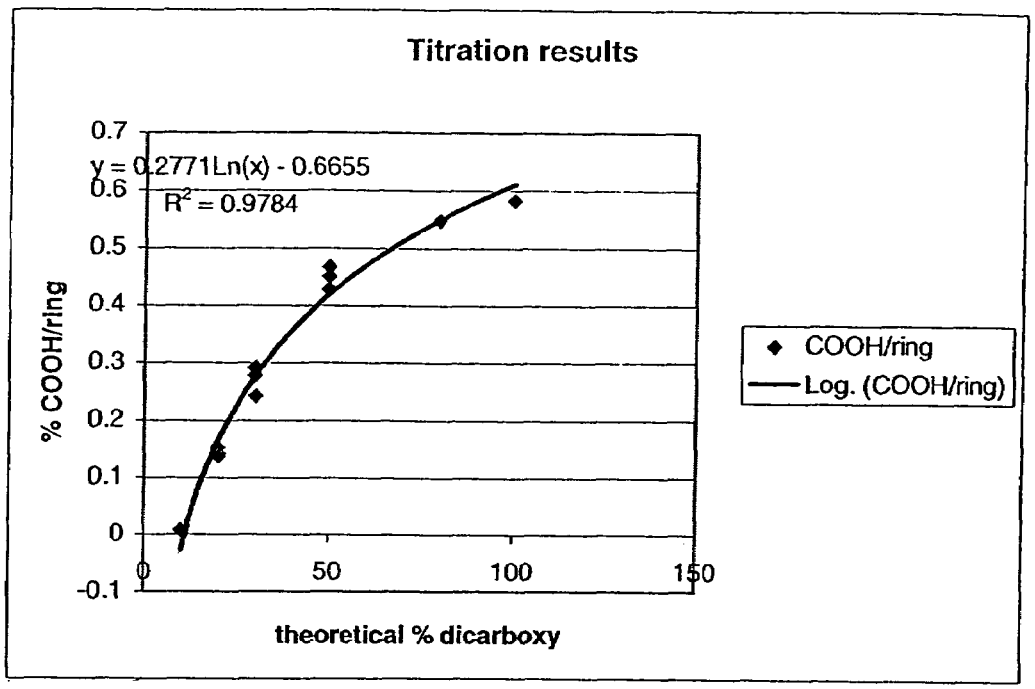
FIG. 8 is a graph showing carboxyl content versus periodate ratio.

Because of the heterogeneity of the material produced using Method 3a for oxidation, titration of those samples was not reproducible. A single sample would have values ranging from 10%-30%. This proved that the material was not being produced in a consistent manner which further confirms that other structures such as hemi-aldols were being formed. Table 4 shows the titration results for the material produced by Method 3b. The standard deviation of titrating a sample in duplicate was from 0.01%-3.1%, which were acceptable values. Also it can be seen from the table that materials produced using the same periodate to starch ratio showed consistent carboxyl content. All of the data presented here were for reactions using 3 hours for the periodate reaction followed by 6 hours for the chlorus acid oxidation with waxy corn starch as the starting material. FIG. 8 graphically shows the relationship between the periodate ratio used and the resulting carboxyl content. A logarithmic dependence can be explained by the fact that as more dialdehyde is the polysaccharide becomes more susceptible to acid hydrolysis breaking the chain into smaller molecular weight chains. These chains are removed during the washing of the material and therefore do not show up in the titration.

TABLE 6

Titration results

| Sample | Periodate ratio % | COOH/ring | Std. Dev. |
|---|---|---|---|
| 44 | 50 | 46.7% | 0.01% |
| 45 | 50 | 45.0% | 0.02% |
| 46 | 30 | 29.1% | 0.03% |
| 47 | 10 | 0.8% | 0.1% |
| 48a | 30 | 27.8% | 2.1% |
| 48b | 30 | 24.2% | 1.8% |
| 49a | 20 | 15.3% | 3.1% |
| 49b | 20 | 12.7% | — |
| 50 | 50 | 42.7% | 1.9% |
| 51a | 20 | 14.3% | 1.5% |
| 51b | 20 | 13.6% | 2.0% |
| 52a | 80 | 54.7% | 1.5% |
| 53a | 100 | 58.2% | 0.0% |

This data deviates from the data presented by Vellaert (Veelaert, S., et al., Polymer 35(23):5091-5097 (1994)), which shows a linear dependence as the stoichiometric amount is increased. This data may be explained by the fact that high amylopectin is being used. This highly branch material may be sterically hindering the oxidation as higher concentrations of periodate are used.

Periodate Oxidation Kinetics Data

Samples were taken during the periodate oxidation of starch and of cellulose at different varying time intervals. The UV spectrophotometer was used to analyze the samples since the periodate has a maximum peak at 223 nm. Data was used from previously obtained periodate data and new data and compared to the model.

A close fitting relationship was found using the Veelaert model. A Runge-Kutta differential equation solver set up on Excel was used to solve for the rate constants. Two separate reactions, one for cellulose and one for starch were compared to the model.

Figure 9:
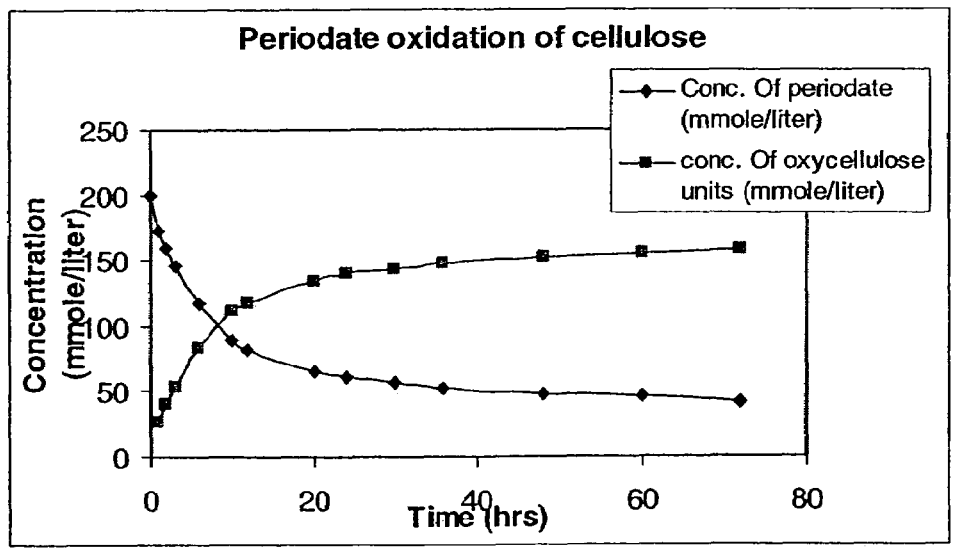
FIG. 9 is a graph showing periodate oxidation of cellulose kinetics.
Figure 10:
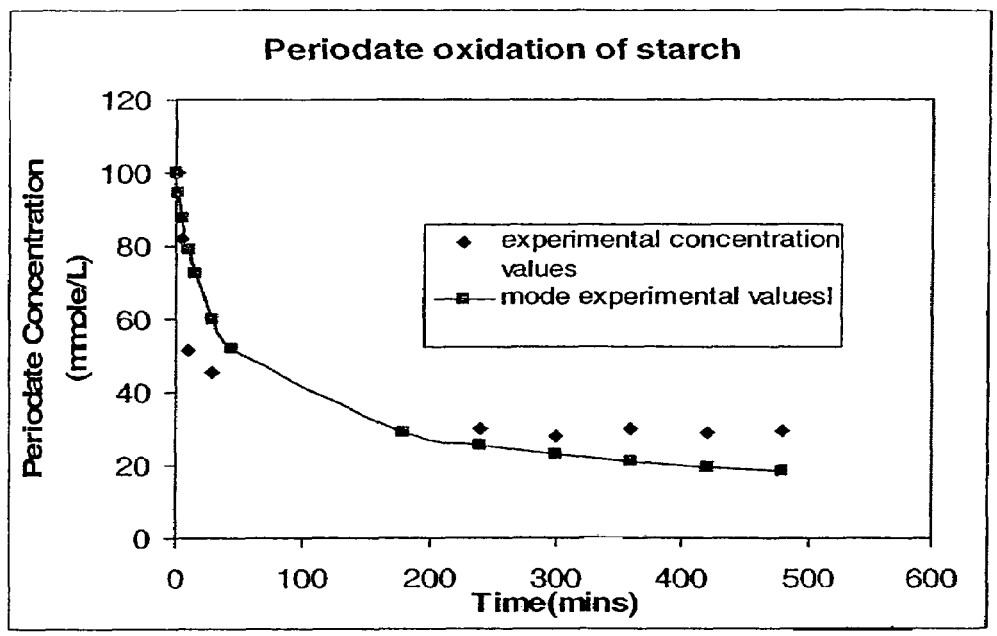
FIG. 10 is a graph showing periodate oxidation of starch kinetics.
Figure 11:
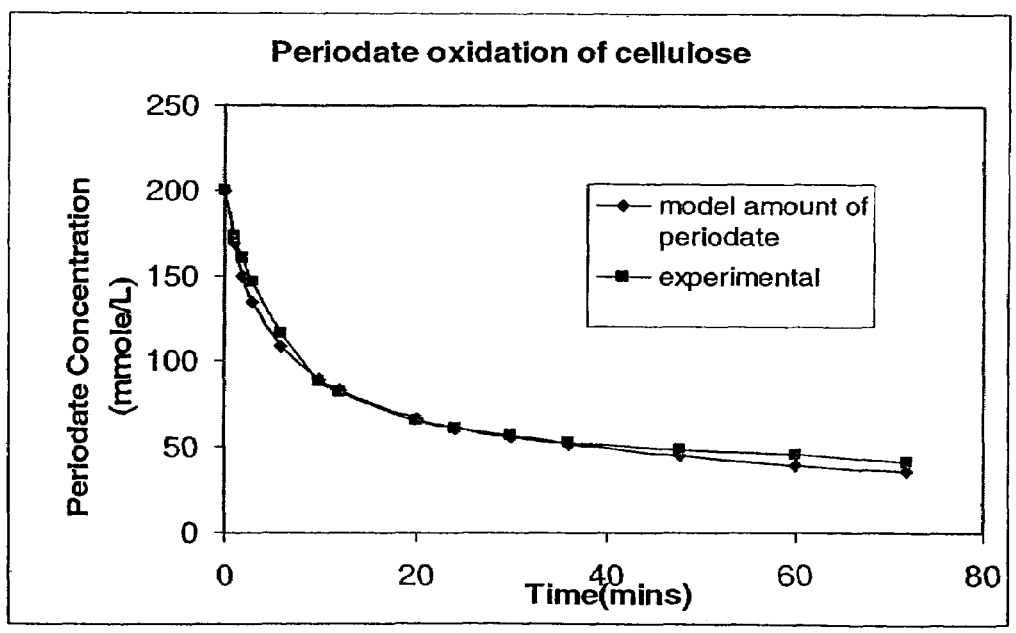
FIG. 11 is a graph showing a comparison of actual and theoretical kinetic data.
Figure 12:
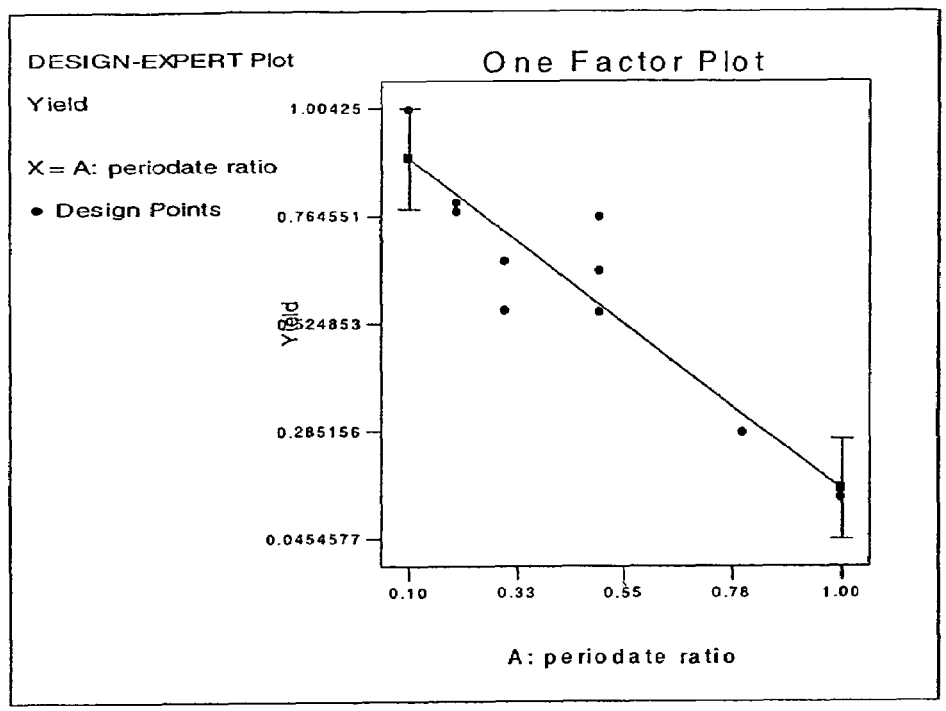
FIG. 12 is a graph showing the relationship between the periodate ratio and the yield.
Figure 13:
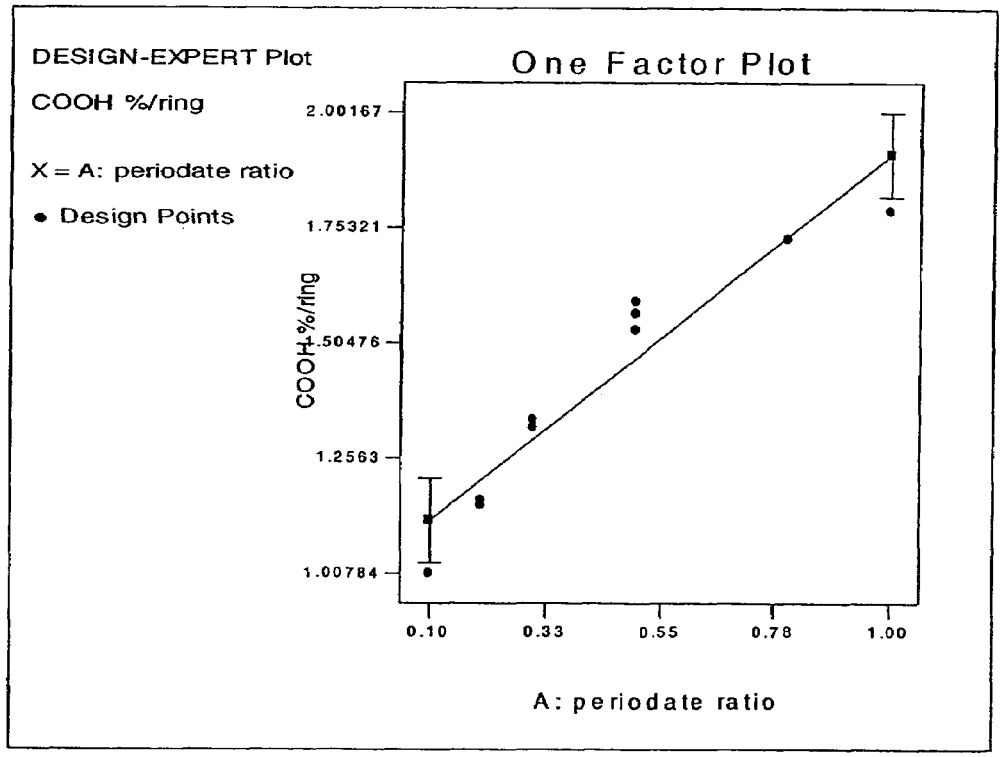
FIG. 13 is a graph showing the relationship between the periodate ratio and the final material acid content.

As can be seen in FIGS. 9, 10 and 11, the models show a close relationship. The rate constants for each are using the endpoint of three hours and the carboxyl content at that point. This introduces error because the assumption is that the dialdehyde is fully oxidized to carboxyl groups.

TABLE 7

Calculated rate constants for the periodate oxidation of starch

| Sample | % dialdehyde | K(calculated) L/mmole/min |
|---|---|---|
| 47 | 10 | 1.500E−08 |
| 49b | 20 | 1.400E−07 |
| 51a | 20 | 1.250E−07 |
| 46 | 30 | 1.300E−07 |
| 48a | 30 | 1.200E−07 |
| 44 | 50 | 3.492E−07 |
| 45 | 50 | 3.205E−07 |
| 50 | 50 | 2.800E−07 |
| 52a | 80 | 8.300E−07 |
| 53a | 100 | 1.350E−06 |

Design of Experiments

Stat-Ease software, Design-Expert 5.0 was used to create a design of experiments to see how the initial periodate ratio affected the product. This was used to optimize the reaction to predict the most desirable product. The final results of this were used as the case that was scaled up as set forth hereinafter. Acid content, overall reaction yield and dispersibility were used to qualify the product. The titration results were used for the acid content. Because of the logarithmic relationship shown in FIGS. 12 to 15, the exponential values of the carboxyl content were used. The yield was calculated by looking at the percentage of the polymeric material left at the end of the reaction compared to the theoretical amount that could be produced and dispersibility was rated on a scale of 0 to 3. On this scale a 3 indicated that within 10 minutes of adding the material to water it appeared completely dispersed, a 2 indicated that in that time frame the majority of the material was swollen and dispersed, a 1 indicated that a majority of the material was not dispersed but at the least the material had swollen considerably and a 0 indicated that there was no visible hydration of the material within the 10 minute timeframe. This is an important factor to consider for manufacturing and formulating of a final product and to ensure that the drug can be uniformly distributed in the matrix. Carboxyl contents and reaction yield showed a statistically significant relationship to the periodate ratio used and the dispersibility show a relationship with a p=0.0761.

Response: Yield
ANOVA for Response Surface Linear Model
Analysis of variance table [Partial sum of squares]

| Source | Sum of Square | DF | Mean Square | F Value | Prob > F |
|---|---|---|---|---|---|
| Model Significant | 0.48 | 1 | 0.48 | 40.98 | 0.0002 |
| A | 0.48 | 1 | 0.48 | 40.98 | 0.0002 |
| Residual | 0.094 | 8 | 0.012 | | |
| Lack of Fit | 0.066 | 4 | 0.016 | 2.30 | 0.2204 not significant |
| Pure Error | 0.029 | 47.166E−003 | | | |
| Cor Total | 0.58 | 9 | | | |

The Model F-value of 40.98 implies the model is significant. There is only a 0.02% chance that a "Model F-Value" this large could occur due to noise.

Values of "Prob>F" less than 0.0500 indicate model terms are significant. In this case A are significant model terms.

Values greater than 0.1000 indicate the model terms are not significant.

If there are many insignificant model terms (not counting those required to support hierarchy), model reduction may improve your model.

Final Equation: Yield=+0.97444−0.81743*periodate ratio

Response: COOH %/ring
ANOVA for Response Surface Linear Model
Analysis of variance table [Partial sum of squares]

| Source | Sum of Square | DF | Mean Square | F Value | Prob > F |
|---|---|---|---|---|---|
| Model Significant | 0.56 | 1 | 0.56 | 70.70 | <0.0001 |
| A | 0.56 | 1 | 0.56 | 70.70 | <0.0001 |
| Residual | 0.063 | 8 | 7.864E−003 | | |
| Lack of Fit | 0.061 | 4 | 0.015 | 28.71 | 0.0033 significant |
| Pure Error | 2.117E−003 | 4 | 5.293E−004 | | |
| Cor Total | 0.62 | 9 | | | |

The Model F-value of 70.70 implies the model is significant. There is only a 0.01% chance that a "Model F-Value" this large could occur due to noise.

Values of "Prob>F" less than 0.0500 indicate model terms are significant. In this case A are significant model terms. Values greater than 0.1000 indicate the model terms are not significant.

Final Equation: COOH %/ring=+1.03430+0.87633*periodate ratio

Response: Dispersibility
ANOVA for Response Surface Linear Model
Analysis of variance table [Partial sum of squares]

| Source | Sum of Square | DF | Mean Square | F Value | Prob > F |
|---|---|---|---|---|---|
| Model Not significant | 3.45 | 1 | 3.45 | 4.16 | 0.0761 |
| A | 3.45 | 1 | 3.45 | 4.15 | 0.0761 |
| Residual | 6.65 | 8 | 0.83 | | |
| Lack of Fit | 3.49 | 4 | 0.87 | 1.10 | 0.4641 not significant |
| Pure Error | 3.17 | 4 | 0.79 | | |
| Cor Total | 10.10 | 9 | | | |

The Model F-value of 4.15 implies there is a 7.61% chance that a "Model F-Value" this large could occur due to noise.

Values of "Prob>F" less than 0.0500 indicate model terms are significant. In this case there are no significant model terms. Values greater than 0.1000 indicate the model terms are not significant. If there are many insignificant model terms (not counting those required to support hierarchy), model reduction may improve your model.

Final Equation: dispersibility=+1.33978+2.18232*periodate ratio

Optimization Results

The following constraints were set to find the optimal periodate ratio used.

Constraints

| Name | Goal | Lower Limit | Upper Limit | Importance |
|---|---|---|---|---|
| Periodate ratio | Is in range | 0.1 | 1 | 3 |
| Yield | Maximize | 0.136 | 1 | 3 |
| COOH %/ring | Is target = 1.398 | 1.007 | 1.789 | 3 |

Solution

| Periodate ratio | Yield | COOH %/ring |
|---|---|---|
| 0.42 | 0.634683 | 1.39854 |

This design of experiments could be expanded in the future to incorporate the release data and calculated diffusion coefficients to develop a predictive model with reactant molarity as the input and diffusion coefficients as the output.

ESEM

Figure 16A:
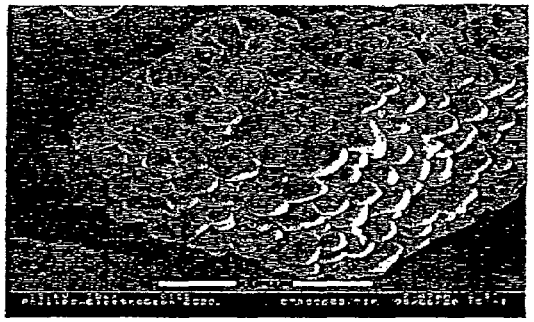
FIGS. 16A to 16E show ESEM scanning electron microscope images of starch (FIGS. 16A to 16C), air dried dicarboxy starch (FIG. 16D) and hydrated dicarboxy starch (FIG. 16E).
Figure 16B:
Figure 16D:
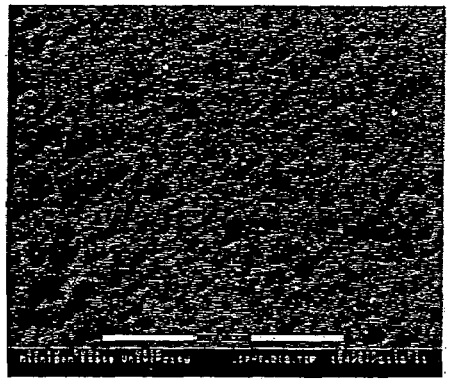
Figure 16C:
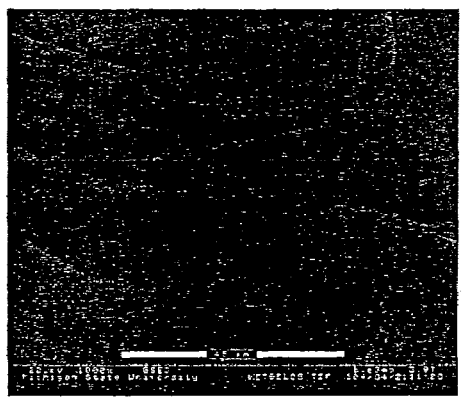
Figure 16E:
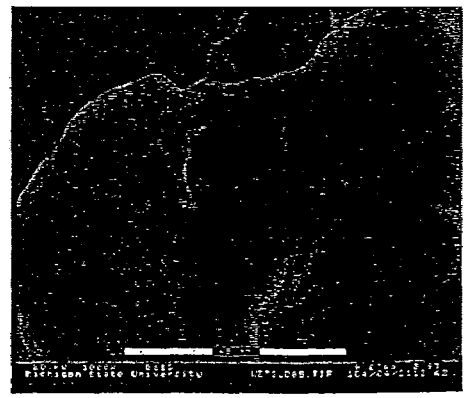

As seen in the ESEM images (see FIGS. 16A to 16E) there is a difference between native starch and the dicarboxy starch. It can be observed that the oxidation process destroys the granular structure of the starch (FIG. 18A), releasing the amylase and amylopectin from the structure creating a smooth and flexible material (FIG. 16D). The ESEM is run under vacuum so it is impossible to observe the hydrated structure. However, the swelling and subsequent dehydration of the material can be observed while the material is first wetted and the vacuum chamber comes to equilibrium (FIG. 16E).

Kinetic Considerations and Scale Up

Figure 17:
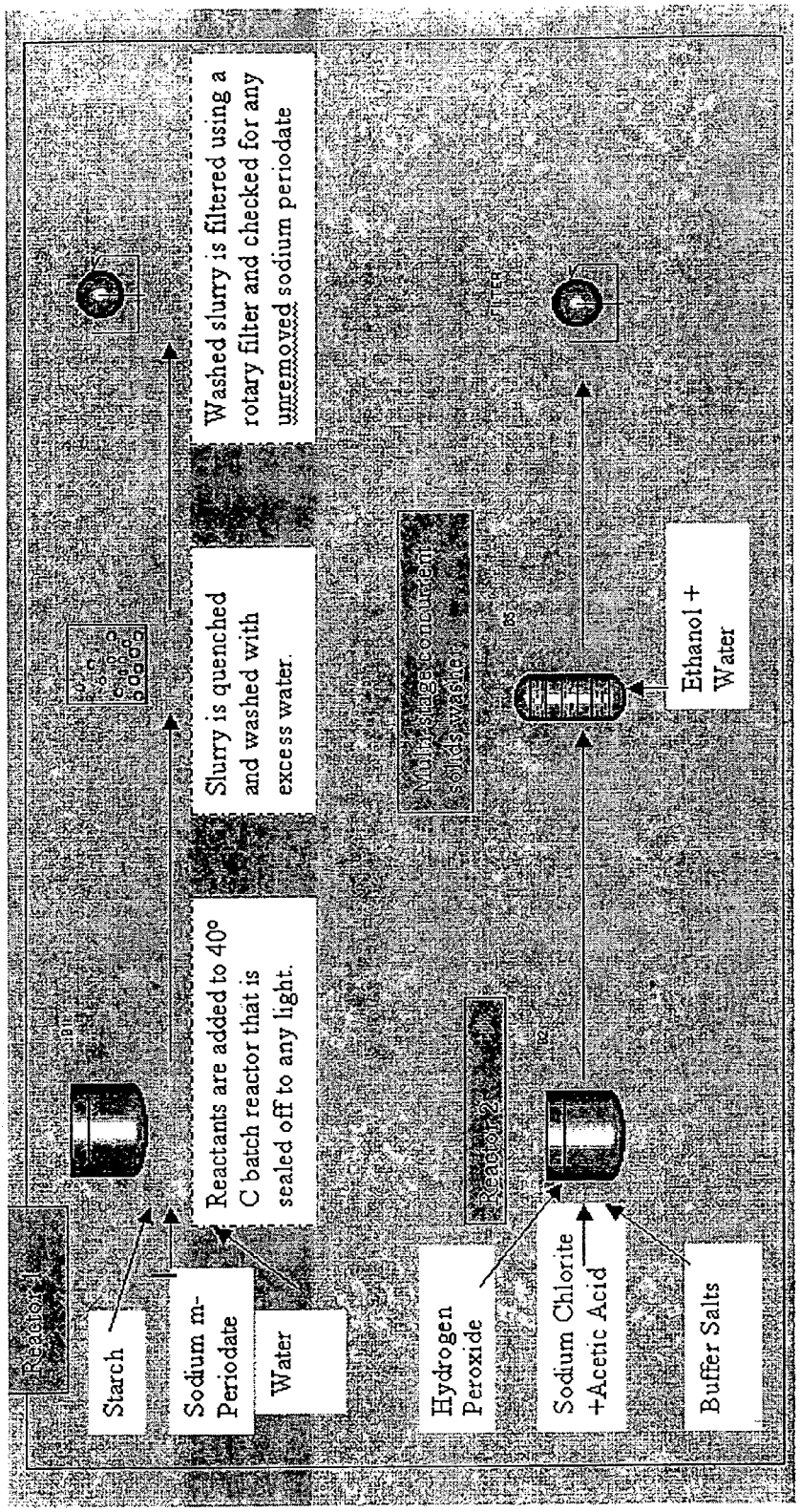
FIG. 17 shows large-scale reaction scheme.

In FIG. 17, a large-scale batch process for the production of the dicarboxy starch is described.

| | |
|---|---|
| Formulated product required/annually | 200000 kg |
| Assume 10,000,000 bottles & 20 ml each | |
| Amount of dicarboxy starch needed/annually | 2000 kg |
| # of batch runs annually | 50 |
| Amount/barch needed for 42% dialdehyde | 40 kg |
| Yield | 63.47% |
| Reactants/batch | |
| Starch | 60.9 kg |
| Sodium m-periodate | 33.8 kg |
| Water | 6282.4 kg |
| Acetic Acid | 13.6 kg |
| Hydrogen Peroxide | 45.1 kg |
| Na-EDTA | 0.8 kg |
| Sodium Chlorite | 42.5 kg |

Reactor 1 is a 500 gallon stainless steel jacketed reactor. Water would be used to heat the reactor to 40° C. The second reactor is a stainless steel 1250 gallon reactor. Chlorine byproduct is controlled and quenched accordingly. The ethanol/water washwater is recycled using a basic distillation column.

A suitable filter that ionically repels the material or at least, not attract it. The iodate can be reoxidized to paraperiodate using sodium hypochlorite which then will release the metaperiodate ion.

Reduction of the aldehyde groups to —OH groups provides hydroxyl moieties in addition to carboxylic moieties.

In vitro UV-Vis Spec

The drug release profiles were conducted using two different set-ups as more equipment became available.

Stir Plate Method

Figure 27:
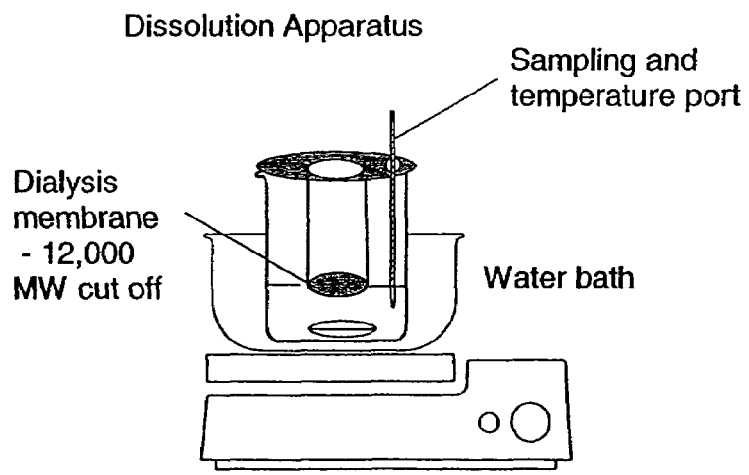
FIG. 27 shows stir plate dissolution system.

In the first set up in FIG. 27, a 15 ml polystyrene centrifuge tube was modified by cutting the tip off and placing a dialysis membrane (Sigma) with a molecular cut-off of 12,000 over the open end. The membrane was secured by wrapping Teflon® taping tightly around the tube. The diffusion surface with this set up was 15 mm and 5 ml of the formulated drug was placed in the tube. Twenty-five milliliters of release medium was placed in a polyethylene cup which was modified by cutting a hole the diameter of the tube in the top along with another hole for sampling and temperature measurements. A 1" stirbar was placed in this cup and the cup was placed in a water bath kept constant at 37° C. on a stir plate. One milliliter samples were taken at time varying intervals and 1 ml of fresh release medium was added to keep the volume constant at 25 ml. The composition of the release medium, simulated tear solution was as follows:

| Simulated Tear Solution I | |
|---|---|
| Sodium Chloride | 0.67 g |
| Sodium bicarbonate | 0.2 g |
| Calcium chloride dehydrate | 0.008 g |
| Water | to 100 g |

This method led to variability because of the variations in the rpm of the stirbar between stir plates. The schematic system is shown in FIG. 27.

USP Dissolution Method

Figure 14:
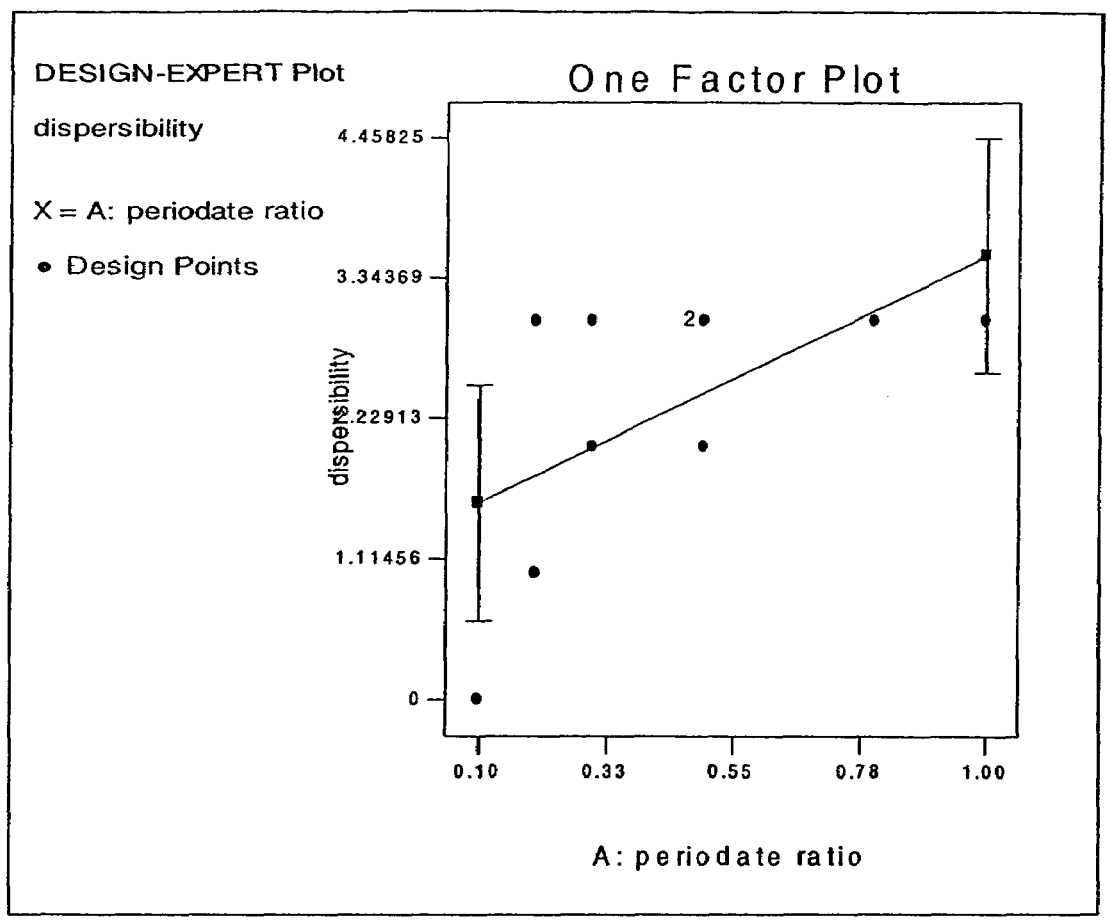
FIG. 14 is a graph showing the relationship between the periodate ratio and the dispersibility of the material.
Figure 15:
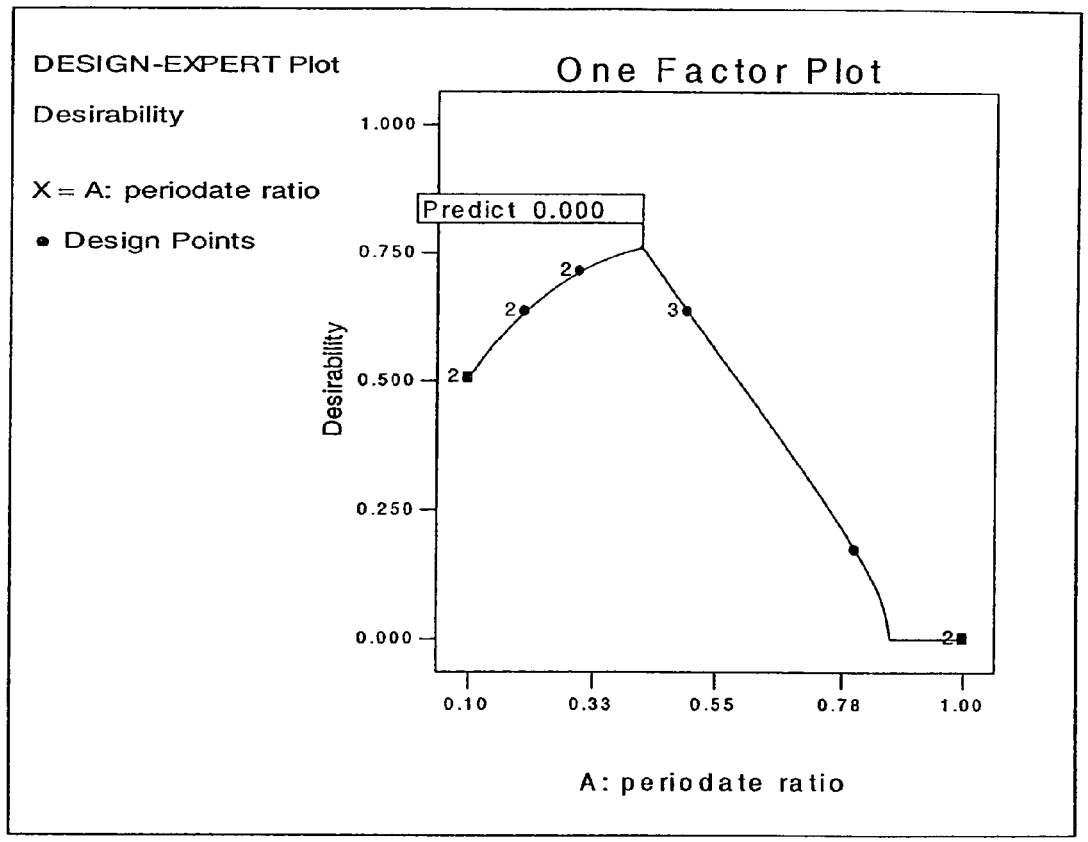
FIG. 15 is a graph showing optimization of the periodate concentration.
Figure 28:
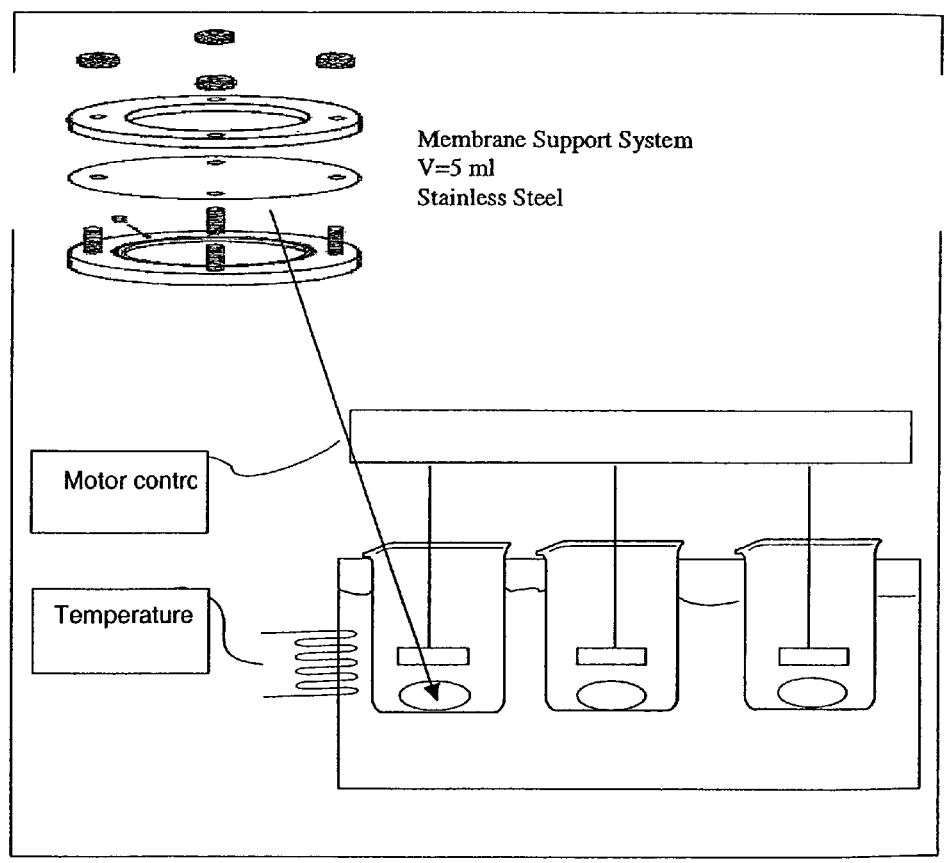
FIG. 28 shows membrane support (above) and dissolution bath for drug release studies.

The second method in FIG. 28 for obtaining release profiles was using a Hanson EZ-lift dissolution system which had 6 separate chambers that were all kept in the same constant temperature bath which was regulated by a feedback loop. Each chamber had a rotating paddle attached to the same drive motor. One liter beakers were used to hold the release medium and they were filled with a specified amount ranging from 400 ml-650 ml. The formulated drug was placed in a well 5 ml with a diameter of 5 cm which was covered with the same dialysis membrane. Again, 1 ml samples were taken at varying intervals; however, the release medium was not replaced in these experiments since the volume difference was considered negligible. A schematic of the system is shown in FIG. 14.

A Perkins-Elmer Lambda 900 Ultraviolet-Visible Spectrophotometer was used to determine the concentration of the drug in the drug release profiles. The strongest peak was at 290 mm and the absorbance there was used to determine the concentration. The UV/VIS integration time was 0.3600 s, and the slit width was set to 2.00 nm. Deionized water was used as the reference, since the tear solution did not contribute to the peak at 290 nm. The software used to obtain the data was UV Winlab for Lambda 900, version 2.90.02.

Drug Release Profiles

Figure 18:
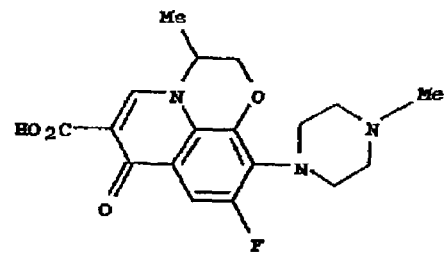
FIG. 18 shows structure of ofloxacin.

Ofloxacin in FIG. 18 is an antibacterial agent belonging to the fluoroquinolone family with molecular weight of 361.37. Of the available fluoroquinolones, ofloxacin is one of only usually given as a single agent and has been shown to have the best aqueous humor penetration. As an ophthalmic formulation, ofloxacin is formulated as a 0.3% w/v solution and goes by the trade name OCUFLOX. According to Allergan's prescribing information packet, OCUFLOX solution is unbuffered and formulated with a pH of 6.4 (range–6.0 to 6.8). It has an osmolality of 300 mOsm/kg. Ofloxacin is a fluorinated 4-quinolone which differs from other fluorinated 4-quinolones in that there is a six member pyridobenzoxazine ring from positions 1 to 8 of the basic ring structure.

Drug Release Results

Figure 19:
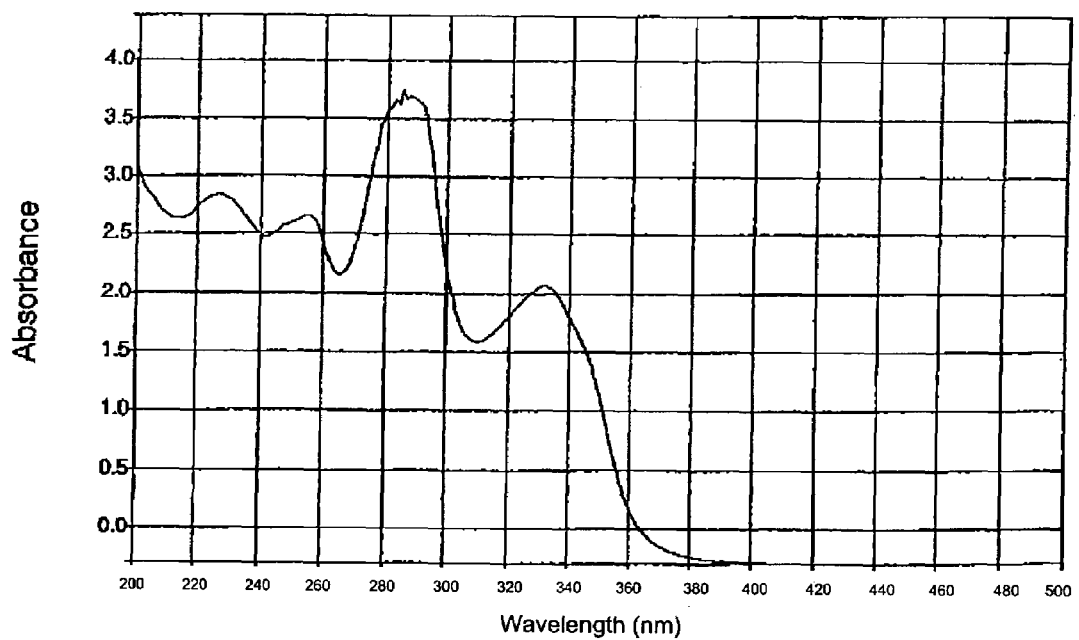
FIG. 19 shows UV-VIS spectrum of ofloxacin.
Figure 20:
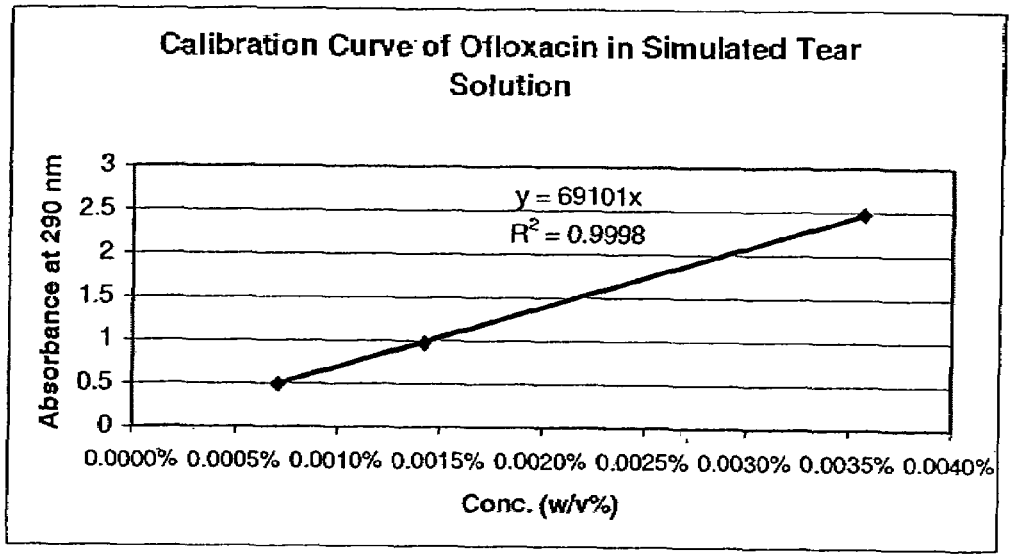
FIG. 20 shows calibration curve for ofloxacin.
Figure 21:
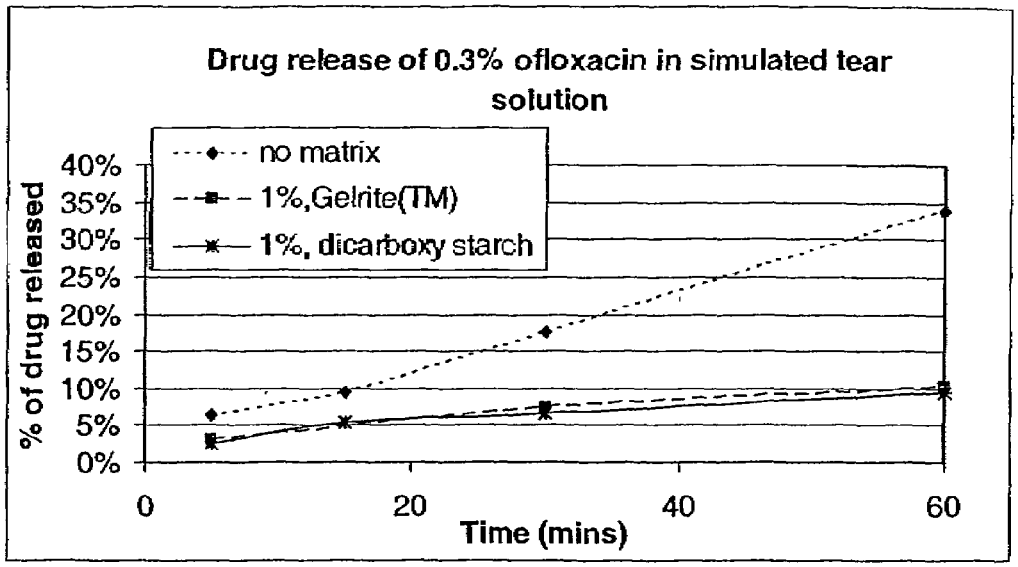
FIG. 21 shows comparison of dicarboxy starch to GEL-RITE.
Figure 22:
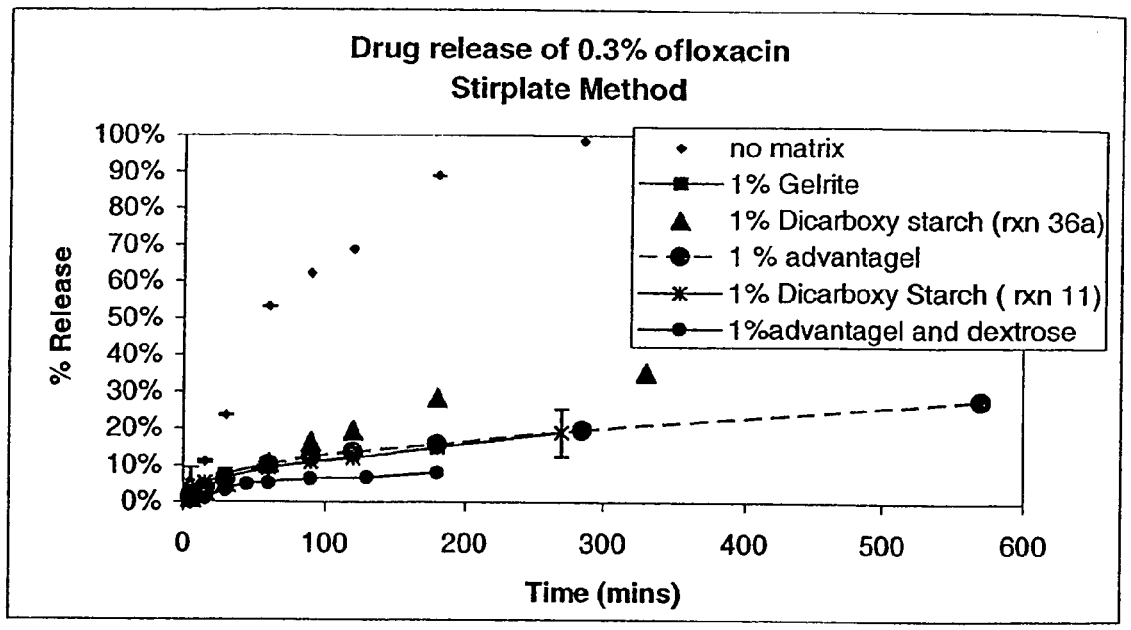
FIG. 22 shows drug release of various materials.
Figure 23:
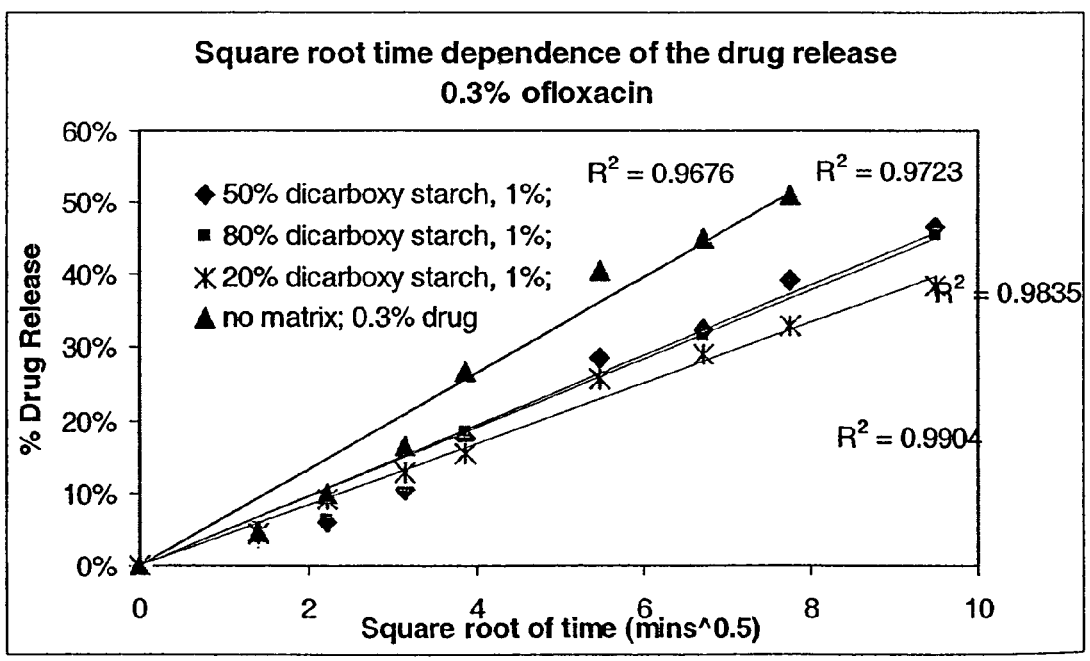
FIG. 23 shows release profiles using USP dissolution system.
Figure 24:
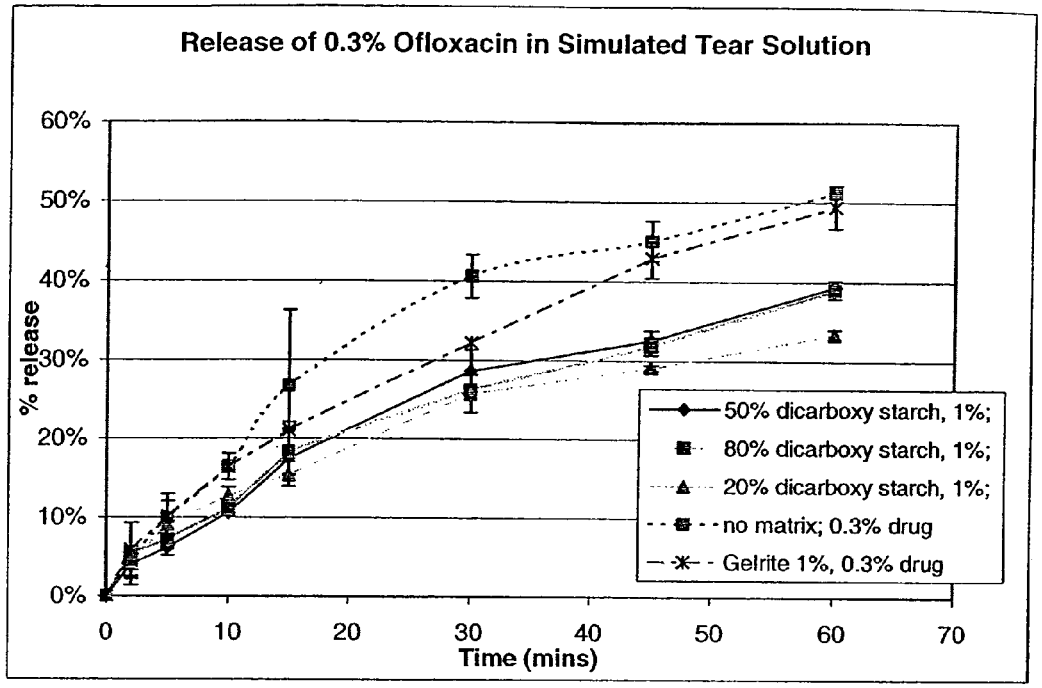
FIG. 24 shows release with varying drug concentration.

The drug release profiles were studied using a Perkin Elmer Lambda 900 ultraviolet-visible spectrophotometer. The absorbance spectrum for the drug ofloxacin can be seen in FIG. 19. The strongest peak at 290 nm was used to determine concentration of ofloxacin as compared to a calibration curve (FIG. 20). The absorbance at concentrations of 0.0036% w/v to 0.00075% w/v was found to be linearly dependent and measurable using the parameters described in the analytical technique chapter. Some of the samples had to be diluted to 1 part sample to 2 parts plain tear solution to have samples in a measurable range. A concentration method was developed to read the output only the absorbance at 290 nm. This eliminated the need of developing full spectra for all of the samples. The calibration confirmed that absorbance was linear with concentration from a range of absorbance from 0-2.5.

The drug release profiles were conducted using the apparatus of FIGS. 27 and 28 and are referred to as the stirplate method and the USP transdermal method.

Stirplate method results

Initially the release of the dicarboxy starch was compared to that of GELRITE to see if it exhibited similar release properties. As seen in FIG. 21 to 24, over a period of one hour the dicarboxy starch and the GELRITE released the ofloxacin in a similar manner.

Results from the USP Method

Figure 25:
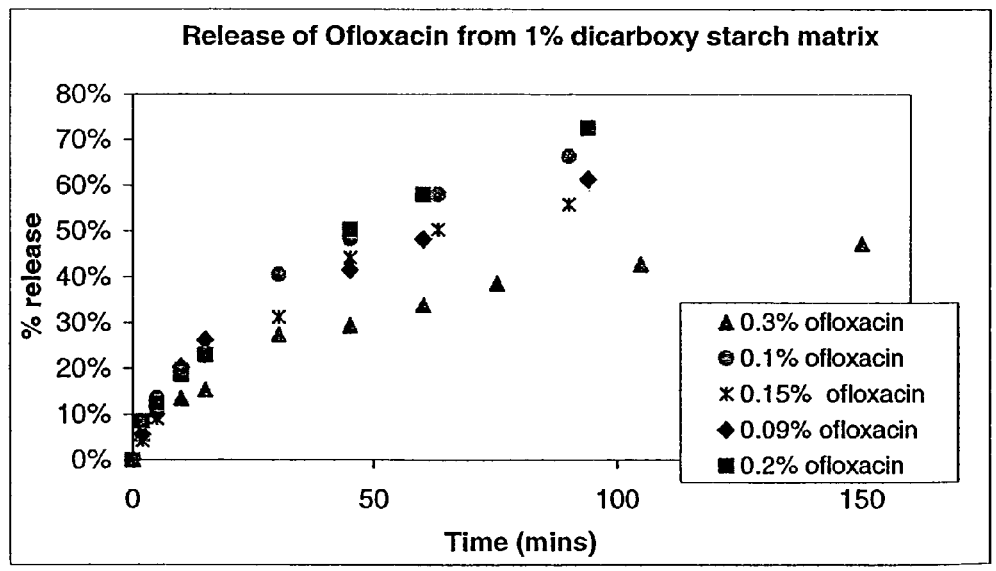
FIG. 25 shows square root time dependence of the ofloxacin.

FIG. 25 shows the release profiles from three (3) different dicarboxy starches (20% dicarboxy, 50% dicarboxy and 80% dicarboxy) compared to the release profile of GELRITE. All were formulated using 1 wt % of the matrix in a phosphate buffer, pH=7.4. There is no statistical difference between the release profiles of the materials with different carboxy concentrations.

Modeling the Diffusion Method

Figure 26:
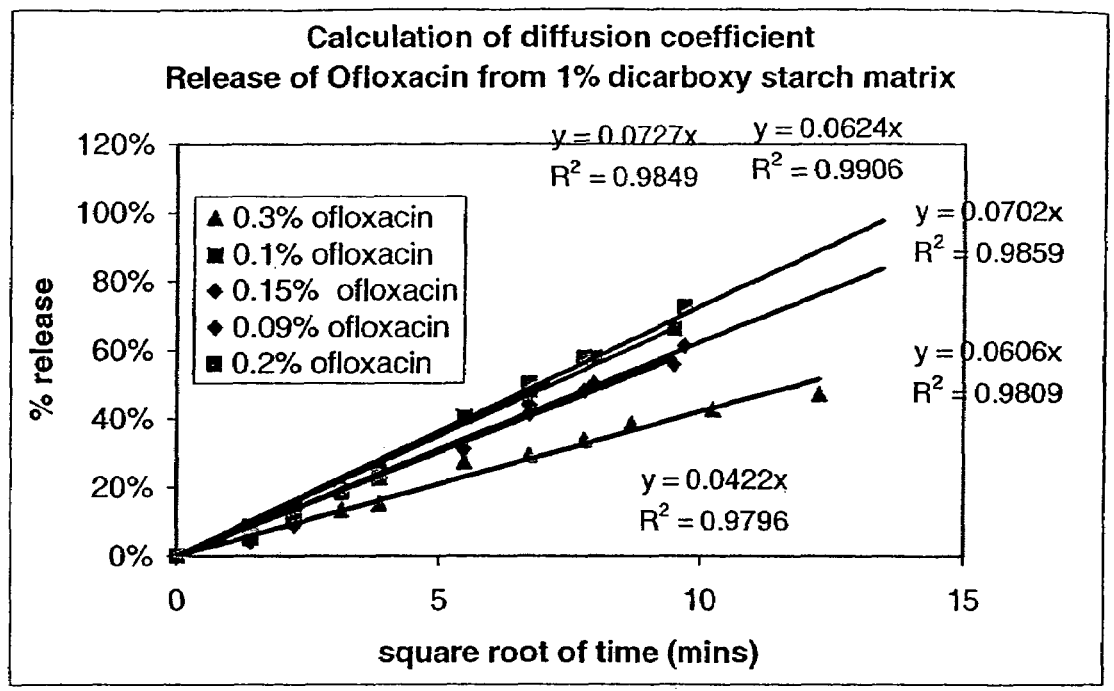
FIG. 26 shows calculation of diffusion coefficient.

The data obtained from the USP dissolution method was used compared to the models predicted by the Higuchi Model. As indicated by the model, the release of the drug from a swollen hydrogel is diffusion controlled and should follow a square root time dependence when the percentage released is less than 60%. As seen in FIG. 26, the drug release is consistent with that model because all experimental data for each of the matrices can be fitted with a linear fit with an $R^2$ value greater than 0.97. The varying slopes of the lines indicate that there are different apparent diffusion coefficients for each of the different materials. This confirms the fact that material can be engineered to change the release profiles. The release profile with no matrix appears linear when plotted against the square root of time, however, there is a higher linear correlation when it is plotted against time which is consistent with standard diffusion through a membrane (Saltzman, M., Drug Delivery:Engineering Principles for Drug Therapy. New York, Oxford University Press (2001)).

Following the Higuchi model for the same material, surface area and volume, the diffusion coefficient should be able to be calculated by changing the concentration of the drug. To calculate this, a formula with 1% of the 20% dicarboxy starch was made up with varying concentrations of ofloxacin. These runs were conducted once each. The percent released was plotted against the square root of time and the slopes of the lines were found. According to Higuchi model, when rearranged for the dimensionless percent released, the slope of the line, y, should be equal to:

$$Y = 2A(D_m/\Pi)^{0.5}$$

Following this equation the slope of the lines showed were equal for the same matrix and release area. As seen in FIG. 26, the slopes vary for each of the release profiles. Since each of these runs were conducted only once, the difference could be due to the number of runs. The 0.3% formulation may becoming close to the solubility limit of the drug in which case the Higuchi model presented would deviate. If the values for the 0.3% value are removed, the average of the slope of the lines becomes 0.0665±95 which is considered a reasonable deviation. Using that number, an apparent diffusion coefficient can be calculated with the answer being 0.000225 cm^2/s.

In conclusion, it appears that the release profiles can be modeled using the Higuchi equation. Monitoring the ofloxacin concentration with the UV-visible spectrophotometer provides a good means to analyze the release profile.

It is intended that the foregoing description be only illustrative of the present invention and that the present invention be limited only by the hereinafter appended claims.

We claim:

1. A method for providing a topical timed release of a fluoroquinolone antibacterial agent for the eyeball of an animal in need thereof, the method comprising:
   (a) providing a composition comprising the fluoroquinolone antibacterial agent and a chemically modified polysaccharide (CMP) random copolymer, the CMP comprising
      (i) saccharide rings having $C_2$ and $C_3$ carbon positions and a bond therebetween, the saccharide rings being linked with
      (ii) ring-opened saccharide units at the bond between the $C_2$ and $C_3$ carbon positions, the ring-opened $C_2$ and $C_3$ carbon positions containing carboxylic acid moieties, water dispersible salts thereof, or combinations thereof;
      wherein the CMP is dispersed in water to form a clear solution as a time-release adjuvant for the fluoroquinolone antibacterial agent; and
   (b) topically providing the composition on the eyeball to provide the timed release.

2. The method of claim 1 wherein at least some of the ring-opened $C_2$ and $C_3$ carbon positions contain hydroxyl groups.

3. The method of claim 1 wherein all of the ring-opened $C_2$ and $C_3$ a carbon positions contain carboxylic acid moieties, water dispersible salts thereof, or combinations thereof.

4. The method of claim 1 wherein the CMP is a random copolymer of linked units of the formula:

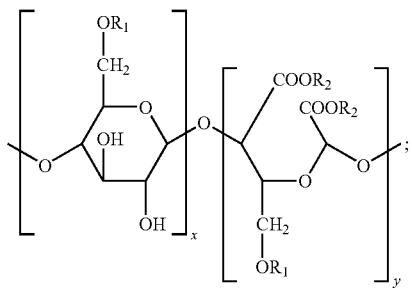

wherein (i) the fraction y of ring-opened saccharide units in the random copolymer is between 10 to 90 mole percent, (ii) $R_1$ is H or COOR where R is alkyl or aryl, and (iii) $R_2$ is H, alkyl or an aryl group containing 1 to 12 carbon atoms.

5. The method of claim 1 wherein the animal is a mammal.

6. The method of claim 5 wherein the mammal is a human.

7. A pharmaceutical composition for topical treatment of the eyeball, the composition comprising:
   (a) a fluoroquinolone antibacterial agent for the eyeball in need of a timed release; and
   (b) a chemically modified polysaccharide (CMP) random copolymer, the CMP comprising
      (i) saccharide rings having $C_2$ and $C_3$ carbon positions and a bond therebetween, the saccharide rings being linked with
      (ii) ring-opened saccharide units at the bond between the $C_2$ and $C_3$ carbon positions, the ring-opened $C_2$ and $C_3$ carbon positions containing carboxylic acid moieties, water dispersible salts thereof, or combinations thereof;

wherein the CMP is water-dispersible to form a clear solution as a time-release adjuvant for the fluoroquinolone antibacterial agent.

8. The composition of claim 7 wherein at least some of the ring-opened $C_2$ and $C_3$ carbon positions contain hydroxyl groups.

9. The composition of claim 7 wherein all of the ring-opened $C_2$ and $C_3$ carbon positions contain carboxylic acid moieties, water dispersible salts thereof, or combinations thereof.

10. The composition of claim 7 wherein the CMP is a random copolymer of linked units of the formula:

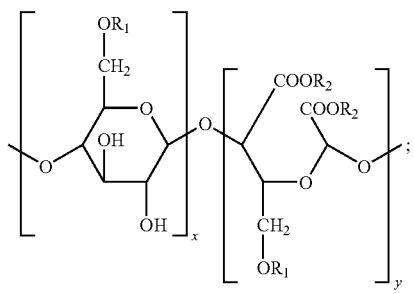

wherein (i) the fraction y of ring-opened saccharide units in the random copolymer is between 10 to 90 mole percent, (ii) $R_1$ is H or COOR where R is alkyl or aryl, and (iii) $R_2$ is H, alkyl or an aryl group containing 1 to 12 carbon atoms.

11. The composition of claim 7 wherein the fluoroquinolone antibacterial agent is ofloxacin.

12. The composition of claim 7 wherein the pharmaceutical composition is dispersed in an aqueous solution and the CMP provides the time-release adjuvant for the fluoroquinolone antibacterial agent.

13. The composition of claim 7 wherein the pharmaceutical composition is water-swellable and capable of forming a swollen hydrogel.

14. The composition of claim 7 wherein the CMP comprises a reaction product of oxidized starch.

15. The method of claim 1 wherein the fluoroquinolone antibacterial agent is ofloxacin.

16. The method of claim 1 wherein the composition is water-swellable and capable of forming a swollen hydrogel.

17. The method of claim 1 wherein the CMP comprises a reaction product of oxidized starch.

18. A pharmaceutical composition for topical treatment of the eyeball, the composition comprising:
(a) a fluoroquinolone antibacterial agent for the eyeball; and
(b) a chemically modified polysaccharide starch (CMP) random copolymer, the CMP comprising
  (i) saccharide rings having $C_2$ and $C_3$ carbon positions and a bond therebetween, the saccharide rings being linked with
  (ii) ring-opened saccharide units at the bond between the $C_2$ and $C_3$ carbon positions, the ring-opened $C_2$ and $C_3$ carbon positions containing carboxylic acid moieties, water dispersible salts thereof, or combinations thereof;

wherein the CMP is water-dispersible to form a clear solution as a time-release adjuvant for the fluoroquinolone antibacterial agent.

* * * * *